US008828331B2

(12) United States Patent
Tajima

(10) Patent No.: US 8,828,331 B2
(45) Date of Patent: Sep. 9, 2014

(54) VARIOUS-SUBSTANCE HOLDER, VARIOUS-SUBSTANCE HOLDER TREATING APPARATUS, AND VARIOUS-SUBSTANCE HOLDER TREATING METHOD

(75) Inventor: Hideji Tajima, Matsudo (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 0 days.

(21) Appl. No.: 13/484,358

(22) Filed: May 31, 2012

(65) Prior Publication Data

US 2012/0252132 A1 Oct. 4, 2012

Related U.S. Application Data

(62) Division of application No. 11/991,506, filed as application No. PCT/JP2006/317337 on Sep. 1, 2006.

(30) Foreign Application Priority Data

Sep. 5, 2005 (JP) ................................. 2005-257059

(51) Int. Cl.
| | | |
|---|---|---|
| G01N 33/00 | (2006.01) | |
| G01N 1/24 | (2006.01) | |
| C12M 1/16 | (2006.01) | |
| G01N 30/60 | (2006.01) | |
| B01L 3/02 | (2006.01) | |
| C12Q 1/68 | (2006.01) | |
| G01N 33/543 | (2006.01) | |
| G01N 35/10 | (2006.01) | |
| G01N 35/00 | (2006.01) | |
| B01L 3/00 | (2006.01) | |

(52) U.S. Cl.
CPC ...... *C12Q 1/6804* (2013.01); *G01N 2035/1055* (2013.01); *G01N 30/6047* (2013.01); *B01L 2300/0636* (2013.01); *B01J 2219/00364* (2013.01); *G01N 2035/00574* (2013.01); *B01L 2300/0838* (2013.01); *B01J 2219/00373* (2013.01); *B01J 2219/005* (2013.01); *G01N 35/10* (2013.01); *B01J 2219/00292* (2013.01); *B01J 2219/00596* (2013.01); *B01J 2219/00576* (2013.01); *B01L 3/0275* (2013.01); *G01N 30/6052* (2013.01); *B01L 2200/0647* (2013.01); *B01L 2300/1827* (2013.01); *B01J 2219/00545* (2013.01); *G01N 33/54313* (2013.01); *B01L 3/502* (2013.01); *G01N 30/6073* (2013.01); *B01J 2219/0052* (2013.01)
USPC ...................... 422/501; 422/82.08; 435/287.2

(58) Field of Classification Search
None
See application file for complete search history.

(56) References Cited

U.S. PATENT DOCUMENTS 5,720,923 A * 2/1998 Haff et al. .................... 422/68.1
5,895,631 A   4/1999 Tajima (Continued)

FOREIGN PATENT DOCUMENTS

EP   1464700 A1   10/2004
EP   1541993 A2   6/2005

(Continued)

OTHER PUBLICATIONS

U.S. Appl. No. 11/664,980, filed Apr. 6, 2007, Hideji Tajima et al.

(Continued)

*Primary Examiner* — P. Kathryn Wright
(74) *Attorney, Agent, or Firm* — Haynes and Boone, LLP

(57) ABSTRACT

A various-substance holder, a various-substance holder treating apparatus, and a various-substance holder treating method are provided which enable the mutual identification of particulate carriers to which various substances are or can be immobilized without the need to arrange the particulate carriers at predetermined positions or in a predetermined order, eliminating the need for time and effort to arrange the various substances at predetermined positions or in a predetermined order to allow treatments to be quickly and easily achieved. The various-substance holder has a plurality of particulate carriers or plural sets of particulate carriers to which plural types of chemical substances are or can be immobilized and a carrier holding portion holding the plurality of particulate carriers or the plural sets of particulate carriers in a substantially stationary state such that the plurality of particulate carriers or the plural sets of particulate carriers can be externally measured.

7 Claims, 13 Drawing Sheets

(56) References Cited

U.S. PATENT DOCUMENTS

| | | | |
|---|---|---|---|
| 6,455,325 B1 | 9/2002 | Tajima | |
| 6,509,193 B1 | 1/2003 | Tajima | |
| 6,660,233 B1* | 12/2003 | Coassin et al. | 422/564 |
| D560,815 S | 1/2008 | Tajima | |
| D561,347 S | 2/2008 | Tajima | |
| D561,906 S | 2/2008 | Tajima | |
| D565,192 S | 3/2008 | Tajima | |
| 2002/0076718 A1* | 6/2002 | Shigeura et al. | 435/6 |
| 2004/0114890 A1* | 6/2004 | Tajima | 385/115 |
| 2005/0124058 A1 | 6/2005 | Tajima | |
| 2005/0130325 A1 | 6/2005 | Oshida et al. | |
| 2006/0154270 A1* | 7/2006 | Tajima | 435/6 |
| 2008/0193995 A1 | 8/2008 | Tajima | |

FOREIGN PATENT DOCUMENTS

| | | | |
|---|---|---|---|
| JP | 03-181853 | | 8/1991 |
| JP | 05-281243 | | 10/1993 |
| JP | 05-506930 | | 10/1993 |
| JP | 08-062225 | | 3/1996 |
| JP | 09-262084 | | 10/1997 |
| JP | 10-117764 | | 5/1998 |
| JP | 10-323177 | | 12/1998 |
| JP | 2000-241436 | | 9/2000 |
| JP | 2000-346842 | | 12/2000 |
| JP | 2001-002695 | | 1/2001 |
| JP | 2001-074756 | | 3/2001 |
| JP | 2001-509256 | | 7/2001 |
| JP | 2002-102681 | | 4/2002 |
| JP | 2002-513936 | | 5/2002 |
| JP | 2002-189033 | | 7/2002 |
| JP | 2002-191351 | | 7/2002 |
| JP | 2003-107083 | | 4/2003 |
| JP | 2003185663 | | 7/2003 |
| JP | 2003-531381 | | 10/2003 |
| JP | 2003-339374 | | 12/2003 |
| JP | 2004020287 | | 1/2004 |
| JP | 2004-033907 | | 2/2004 |
| JP | 2004-061397 | | 2/2004 |
| JP | 2004-294316 | | 10/2004 |
| JP | 2004-359201 | | 12/2004 |
| JP | 2004-359202 | | 12/2004 |
| JP | 2005-030906 | | 2/2005 |
| JP | 2005172699 | | 6/2005 |
| JP | 2005-278437 | | 10/2005 |
| JP | 2006-24502 | | 9/2006 |
| JP | 2006-24503 | | 9/2006 |
| JP | 2006-24504 | | 9/2006 |
| JP | 2006-24505 | | 9/2006 |
| JP | 2006-24527 | | 9/2006 |
| WO | WO 00/67893 | | 11/2000 |
| WO | WO 03/004160 | | 1/2003 |
| WO | WO 2003/060115 | | 7/2003 |
| WO | WO-2004068144 | * | 8/2004 |
| WO | WO 2006-038643 | | 4/2006 |
| WO | WO 2006/062235 | | 6/2006 |
| WO | WO 2006/062236 | | 6/2006 |

OTHER PUBLICATIONS

U.S. Appl. No. 11/792,783, filed Jun. 8, 2007, Hideji Tajima.

U.S. Appl. No. 11/792,835, filed Jun. 8, 2007, Hideji Tajima.

U.S. Appl. No. 11/794,828, filed Jul. 3, 2007, Hideji Tajima.

U.S. Appl. No. 29/303,831, filed Jan. 19, 2008, Hideji Tajima.

International Searching Authority "Written Opinion," Jan. 24, 2006, 4 pages, International Serial No. PCT/JP2005/018419, Japanese Patent Office.

International Searching Authority "International Search Report," Jan. 24, 2006, 2 pages, International Serial No. PCT/JP2005/018419, Japanese Patent Office.

International Searching Authority "International Search Report," Feb. 20, 2006, 4 pages, International Serial No. PCT/JP2005/022775, Japanese Patent Office.

International Searching Authority "Written Opinion," Feb. 28, 2006, 5 pages, International Serial No. PCT/JP2005/022775, Japanese Patent Office.

International Searching Authority "Written Opinion," Mar. 7, 2006, 5 pages, International Serial No. PCT/JP2005/022776, Japanese Patent Office.

International Searching Authority "International Search Report," Mar. 7, 2006, 4 pages, International Serial No. PCT/JP2005/022776, Japanese Patent Office.

International Preliminary Examination Authority, "International Preliminary Examination Report on Patentability," Oct. 3, 2006, 13 pages, International Serial No. PCT/JP2005/018419, Japanese Patent Office.

International Preliminary Examination Authority, "International Preliminary Examination Report on Patentability," Nov. 29, 2006, 8 pages, International Serial No. PCT/JP2005/022776, Japanese Patent Office.

International Preliminary Examination Authority, "International Preliminary Examination Report on Patentability," Dec. 12, 2006, 11 pages, International Serial No. PCT/JP2005/022775, Japanese Patent Office.

Mark Cavanna, "Notice of Allowability," Aug. 13, 2007, 5 pages, Design U.S. Appl. No. 29/277,775, U.S. Patent and Trademark Office.

Mark Cavanna, "Notice of Allowance and Fee(s) Due," Aug. 30, 2007, 3 pages, Design U.S. Appl. No. 29/277,775, U.S. Patent and Trademark Office.

Mark Cavanna, "Supplemental Notice of Allowability," Nov. 21, 2007, 4 pages, Design U.S. Appl. No. 29/277,775, U.S. Patent and Trademark Office.

Mark Cavanna, "Notice of Allowability," Aug. 13, 2007, 7 pages, Design U.S. Appl. No. 29/277,777, U.S. Patent and Trademark Office.

Mark Cavanna, "Notice of Allowance and Fee(s) Due," Aug. 30, 2007, 3 pages, Design U.S. Appl. No. 29/277,777, U.S. Patent and Trademark Office.

Mark Cavanna, "Supplemental Notice of Allowability," Nov. 21, 2007, 5 pages, Design U.S. Appl. No. 29/277,777, U.S. Patent and Trademark Office.

Mark Cavanna, "Notice of Allowability," Aug. 13, 2007, 7 pages, Design U.S. Appl. No. 29/277,778, U.S. Patent and Trademark Office.

Mark Cavanna, "Notice of Allowance and Fee(s) Due," Aug. 31, 2007, 3 pages, Design U.S. Appl. No. 29/277,778, U.S. Patent and Trademark Office.

Mark Cavanna, "Supplemental Notice of Allowability," Nov. 21, 2007, 6 pages, Design U.S. Appl. No. 29/277,778, U.S. Patent and Trademark Office.

Mark Cavanna, "Notice of Allowability," Aug. 13, 2007, 7 pages, Design U.S. Appl. No. 29/277,779, U.S. Patent and Trademark Office.

Mark Cavanna, "Notice of Allowance and Fee(s) Due," Sep. 7, 2007, 3 pages, Design U.S. Appl. No. 29/277,779, U.S. Patent and Trademark Office.

Mark Cavanna, "Supplemental Notice of Allowability," Nov. 21, 2007, 7 pages, Design U.S. Appl. No. 29/277,779, U.S. Patent and Trademark Office.

Mark Cavanna, "Office Action," Aug. 22, 2007, 7 pages, Design U.S. Appl. No. 29/277,780, U.S. Patent and Trademark Office.

Mark Cavanna, "Notice of Allowability," Oct. 29, 2007, 1 page, Design U.S. Appl. No. 29/277,780, U.S. Patent and Trademark Office.

Mark Cavanna, "Notice of Allowance and Fee(s) Due," Dec. 10, 2007, 3 pages, Design U.S. Appl. No. 29/277,780, U.S. Patent and Trademark Office.

Mark Cavanna, "Supplemental Notice of Allowability," Feb. 8, 2008, 5 pages, Design U.S. Appl. No. 29/277,780, U.S. Patent and Trademark Office.

Japanese Patent Office, "International Search Report," International Patent Application No. PCT/JP2006/300064, Apr. 4, 2006, 7 pages.

International Searching Authority, "Written Opinion," Oct. 3, 2006, 3 pages, International Serial No. PCT/JP2006/317337.

International Searching Authority, "International Search Report," Oct. 3, 2006, 2 pages, International Serial No. PCT/JP2006/317337.

(56) References Cited

OTHER PUBLICATIONS

International Preliminary Examination Authorty, "International Preliminary Report on Patentability," 10 pages, Jan. 8, 2008, International Serial No. PCT/JP2006/317337.
Office Action mailed Apr. 18, 2011, by the USPTO, in connection with U.S. App No. 11/991,506.
Office Action mailed Jul. 5, 2011, by the USPTO, in connection with U.S. App No. 11/991,506.
Office Action mailed Mar. 21, 2011, by the USPTO, in connection with U.S. App No. 11/991,506.
Advisory Action mailed May 25, 2012, by the USPTO, in connection with U.S. App No. 11/991,506.

* cited by examiner (a)

(b)

VARIOUS-SUBSTANCE HOLDER, VARIOUS-SUBSTANCE HOLDER TREATING APPARATUS, AND VARIOUS-SUBSTANCE HOLDER TREATING METHOD

CROSS REFERENCE

This application is a division of U.S. patent application Ser. No. 11/991,506, filed Sep. 1, 2006, which is a United States national phase application of international patent application number PCT/JP2006/317337, filed Sep. 1, 2006, which claims priority to Japanese patent application number 2005-257059, filed Sep. 5, 2005, the disclosures of which are incorporated herein by reference.

TECHNICAL FIELD

The present invention relates to a various-substance holder, a various-substance holder treating apparatus, and a various-substance holder treating method.

BACKGROUND ART

To be subjected to a series of reaction treatments using a large number of reagents and substances, a target substance to be checked is conventionally bonded to micro carriers such as beads before being accommodated in a test tube. Various reagents are subsequently poured into the test tube. The carriers are separated from the substance using a certain method and are then moved to another container. Another reagent or the like is further poured into the test tube, or the test tube is heated. For example, if the carriers are a magnetic substance, a magnetic field is used to attract the carriers to an inner wall of the test tube for separation.

In a treatment of checking a target substance using a planar carrier such as a prepared slide to which for example, various oligonucleotides are immobilized, the base sequence structure of the target substance has been examined by performing a series of reaction treatments of moving the carrier through a suspension in which the leveled target substance is suspended, dispensing various reagents to the carrier itself, moving the carrier itself through a cleaning fluid, and moving the carrier to a measurement position in a measuring machine in order to measure luminescence.

Disadvantageously, achieving these treatments requires the separation and transfer of the carrier itself, complicating the treatments and requiring much effort and time. In particular, when the carrier itself is transferred and if the transfer is manually performed, a heavy burden may be imposed on the user and cross contamination may occur. Furthermore, if the carrier itself is mechanically transferred, a large-scale apparatus is required. Additionally, if a nonmagnetic carrier is separated, the separation needs to be performed depending on the size or specific gravity of the carrier. This complicates the treatments and requires much effort and time.

On the other hand, reaction treatments have been performed using, instead of the test tube or the planar carrier, a pipette apparatus having a pipette tip having a liquid passage through which liquid can pass, a nozzle in which the pipette tip is installed, a magnetic device that applies a magnetic field to the liquid passage in the pipette tip, and a suction and discharge mechanism that sucks a fluid into the pipette tip and discharges the fluid from the tip. This method sucks a suspension in which a large number of magnetic particles holding various substances on surfaces thereof are suspended. During the suction, a magnetic field is applied to the liquid passage in the pipette tip. The magnetic particles can thus be efficiently attracted to the liquid passage for separation or the like. However, since the magnetic particles can pass through the liquid passage, a magnetic field needs to be applied to the pipette tip to attract the magnetic particles to an inner wall of the pipette tip in order to hold the magnetic particles in the pipette tip. Thus, the treatments require a combination of the control of the suction and discharge, the control of the attraction by the magnetic field, and the control of movement of the pipette tip. Furthermore, if the carrier is nonmagnetic particles, the apparatus disadvantageously fails to separate the carriers (Patent Documents 1 to 3).

In another conventional apparatus, beads with probes are held in a small hole and then moved to a capillary or a groove. The beads are then arranged according to the types thereof and in a specified order to produce a probe bead array. Alternatively, the beads with the probes are poured into a liquid flow in a specified order and thus housed in the groove or the capillary to produce a probe array with the beads arranged in the specified order (Patent Document 4).

Another system or method for detecting a large number of analytes in a fluid sample to analyze and display the analytes in real time has at least one light source and at least one photodetector and includes an optical assembly located on substantially the same plane. The system or method can communicate with a computer and includes a memory medium which is readable by the computer and which stores commands from the computer. The commands involve treatments on a certain biological sample using a flow analyzer and determination of the presence and amount of at least one analyte of interest in the biological sample which determination is made substantially simultaneously with the treatment step (Patent Document 5).

However, since the particles are very small for human beings to handle (for example, several tens of μm to several mm), disadvantageously, the accurate alignment of the large number of particles in the groove or capillary in the specified order may require much effort and time and may be difficult to handle. Another problem is that the incorrect sequence of the particles may prevent accurate association. Furthermore, if particles suspended in a liquid are subjected to a specified flow speed so as to migrate through a flow tube and are measured by a photodetector provided outside the flow tube, the particles need to be strictly traced and measured one by one. This may disadvantageously complicate the apparatus structure and require complicated control.

[Patent Document 1] Japanese Patent No. 3115501
[Patent Document 2] WO 96/29602
[Patent Document 3] WO 97/44671
[Patent Document 4] Japanese Patent Laid-Open No. 2000.
[Patent Document 5] National Publication of International Patent Application No. 14-534657

DISCLOSURE OF THE INVENTION

Thus, a first object of the present invention is to provide a various-substance holder, a various-substance holder treating apparatus, and a various-substance holder treating method which enable the mutual identification of a plurality of particulate carriers to which various substances such as biological substances are or can be immobilized, without the need to arrange the particulate carriers at predetermined positions in a predetermined order according to the various substances, eliminating the need to arrange the various substances to allow treatments to be quickly and easily performed.

A second object of the present invention is to provide a various-substance holder, a various-substance holder treating apparatus, and a various-substance holder treating method which hold the particulate carriers in a substantially stationary state without the need to immobilize the particulate carriers by attraction or suction or to move the particulate carriers by applying a fluid force thereto, facilitating handling and measurement of the particulate carriers and increasing accuracy to allow treatments to be performed using a small-scale apparatus configuration.

A third object of the present invention is to provide a various-substance holder, a various-substance holder treating apparatus, and a various-substance holder treating method which are suited for automation because of the capability of consistently and automatically performing a series of treatments of various substances such as immobilization, transfer, reaction, and measurement thereof using the particulate carriers.

A fourth object of the present invention is to provide a various-substance holder, a various-substance holder treating apparatus, and a various-substance holder treating method which allow treatments of the particulate carriers such as immobilization thereof to be performed in an area different from that in which measurements are made, enabling the particulate carriers to be easily introduced, held, and measured to allow the improvement of efficiency, reliability and credibility of the treatment.

A fifth object of the present invention is to provide a various-substance holder, a various-substance holder treating apparatus, and a various-substance holder treating method which enable immobilization, labeling, and dissociation of particulate carriers and measurement of the particulate carriers held in the substantially stationary state to be easily repeated any number of times, increasing treatment efficiency.

A first invention provides a various-substance holder comprising a plurality of particulate carriers or plural sets of particulate carriers to which plural types of chemical substances are or can be immobilized and a carrier holding portion holding the plurality of particulate carriers or the plural sets of particulate carriers in a substantially stationary state such that the plurality of particulate carriers or the plural sets of particulate carriers can be externally measured, wherein each of the plurality of particulate carriers or at least one of the particulate carriers belonging to the plural sets of the particulate carriers are labeled according to types of the chemical substances or for each of the particulate carriers or each set of the particulate carriers so as to be mutually identifiable before the particulate carriers are introduced and held in the carrier holding portion.

Here, the "plural types of chemical substances", that is, various substances, are chemical substances such as plural types of biological substances, for example, genetic substances such as nucleic acids, biological macromolecules or small molecules such as proteins, sugars, sugar chains, and peptides. For example, the biological substance is used as a ligand to detect a binding to another biological substance which can bind to the above-described biological substance and which serves as a receptor, to capture, separate, or extract the another biological substance. The receptor includes genetic substances such as nucleic acids, and biological substances such as proteins, sugar chains, and peptides each of which can bind to each of the genetic substances such as the nucleic acids or the proteins, sugar chains, and peptides described above. Living organisms such as cells, viruses, or plasmids themselves may be used as or in place of the biological substances.

The term "immobilization" refers to bonding of at least one of the plural types of chemical substances to the particulate carriers directly or indirectly via another type of substance for association. The bonding includes covalent bonding and chemical adsorption, as well as physical attraction, hydrogen bonding, and bonding based on an electric interaction. Alternatively, a binding substance in the particulate carriers is immobilized to the various substances through a specific reaction or by another method. Furthermore, the capability of reaction or bonding with the various substances may be improved by forming the particulate carriers using a porous member, a recessed and protruding member, or a fibrous member. For the immobilization, the particulate carriers are allowed to, for example, express or generate a functional group. The functional group used to immobilize the biological substances is expressed or generated by hydrolyzing a peptide bond in silk or the like, nylon (3-nylon, 6-nylon, 6,6-nylon, 6,10-nylon, 7-nylon, 12-nylon, or the like), or a wholly aromatic polyamide such as PPTA (polyparaphenylene terephthalamide), which is made up of a "polyamide-based polymer", or in a hetero ring-containing aromatic polymer or the like. The function group that can bind to the biological substances is, for example, a carboxyl group-COOH, an amino group-NH.sub.2, or a group derived therefrom. Here, the diameter of each pore suitable for immobilization of the biological substances is, for example, at most several micrometers.

The "particulate carrier" is a particulate solid having a size allowing the particulate carrier to be introduced and held in the carrier holding portion. The particulate carrier is 0.1 mm to several mm across or has a diameter of 0.1 mm to several mm. A space portion of the various-substance holder capable of holding the particulate carriers, in which portion the particulate carriers are held, has a volume of, for example, several microliters to several hundred microliters provided that the held particulate carriers are excluded from the space portion. The particulate carrier may be solid or hollow so that a substance can be accommodated inside the carrier.

A raw material for the "particulate carrier" is insoluble in a liquid sample. Examples of the raw material include inorganic substances, for example, metals, semiconductors, metalloids, metal compounds such as metal oxides, ceramics, glass, and silica, and organic substances including rubbers, latex, or resins such as polystyrene, polypropyrene, polyester, and acrylic, polymer substances, for example, fiber substances such as cellulose and nylon described above, and natural substances, for example, natural fibers such as silk. More specifically, the resins include polymers obtained by using one of the monomers shown below or combining at least two types of the monomers. Examples of the monomer include aromatic vinyl compounds such as a-methylstyrene, acrylates or methacrylates such as methyl(metha)acrylate and ethyl(metha)acrylate, vinyl cyanide compounds such as acrylonitrile, multifunctional (metha)acrylate compounds such as ethylene glycol diacrylate and ethylene glycol dimethacrylate, and multifunctional aromatic vinyl compounds such as divinyl benzene. These monomers may be used with a monomer having a functional group such as acrylic acid, methacrylic acid, styrenesulfonic acid, or vinyl pyridine. Furthermore, examples of the fiber substance or the like include polysaccharide cross linked substances such as agarose, dextran, cellulose, and carboxymethyl cellulose, and protein cross linked substances such as methylated albumin, gelatine, collagen, and casein. Alternatively, the fibrous material or the like may be silk or the like, nylon (3-nylon, 6-nylon, 6,6-nylon, 6,10-nylon, 7-nylon, 12-nylon, or the like), or PPTA (polyparaphenylene terephthalamide), or a wholly aromatic polyamide, which is made up of a "polyamide-containing polymer", or a hetero ring-containing aromatic polymer.

Alternatively, the particulate carrier may be, for example, a fibrous substance, a porous substance, or a gelled substance.

The "set of particulate carriers" is a collection of particulate carriers to which at least two particulate carriers belong. The particulate carriers belonging to the particular set are identified on the basis of the predetermined number of particulate carriers, a predetermined distance between the particulate carriers, a predetermined range in which the particulate carriers are positioned, or a predetermined boundary, film, or case surrounding the particulate carriers belonging to the set. Thus, the set of particulate carriers can be handled as one particulate carrier. Furthermore, required functions may be distributed among the particulate carriers so that some of the particulate carriers provide a function of allowing the various substances to be immobilized, some provide a function of allowing the various substances to be identified, and the others are used for a different purpose (these particulate carriers show the boundary between adjacent sets or blocks light or the like in order to prevent the mixture of light or the like resulting from labeling). This facilitates handling of the particulate carriers. Moreover, various other functions may be added to the particulate carriers. Additionally, provided that each set of particulate carriers can be definitely identified, the number of particulate carriers belonging to the set can be optionally set. Consequently, the present invention is easily expandable and can exhibit diversity and flexibility.

The expression "can be externally measured" refers to the capability of externally determining how the particulate carriers held in the carrier holding portion are labeled.

The expression "holds the plurality of particulate carriers or the plural sets of the particulate carriers in the substantially stationary state" refers to the state in which each of the particulate carriers is kept almost stationary with respect to the other particulate carriers, the carrier holding portion, or an introduced liquid instead of moving freely in the carrier holding portion. However, the particulate carrier need not be completely immobilized.

Since "each of the plurality of particulate carriers or at least one of the particulate carriers belonging to the plural sets of the particulate carriers is labeled according to the type of each of the chemical substances or for each of the particulate carriers or each set of the particulate carriers so as to be mutually identifiable before the particulate carriers are introduced and held in the carrier holding portion", an array need not be formed in which the particulate carriers cannot be mutually identified on the basis of positional information (including ordinal information) until the particulate carriers are introduced and held in the carrier holding portion in a predetermined sequence.

The expression "the particulate carriers are labeled so as to be mutually identifiable" means that identifiable labeling elements are held in or bonded or immobilized to the particulate carriers themselves or the particulate carriers themselves are processed or formed so as to be identifiable. This means that the cause of the labeling lies in the particulate carriers and does not lie outside the particulate carriers as in the case of the sequence or positions of the particulate carriers. The particulate carriers are labeled with, for example, shaping the particulate carriers like spheres, cubes, cylinders, quadrangular prisms, cones, or pyramids or such that the carriers have recesses and protrusions, varying the size of the particulate carriers, applying various pigments to the particulate carriers, or providing the particulate carriers with labeling elements such as luminescent substances, for example, various fluorescent substances, phosphorescent substances, or chemiluminescent substances, radioactive substances emitting electromagnetic waves of various wavelengths, including infrared rays, ultraviolet rays, and electric waves of various wavelengths, or magnetic substances with various magnetic intensities. In this case, the labeling includes the provision of the labeling elements such as the luminescent substances, the radioactive substances of the various electromagnetic waves, or the magnetic substances not only on the surface of the particulate carriers but also inside the particulate carriers. If the labeling elements are provided inside the particulate carriers, each of the particulate carriers may be formed into a particulate case or film that is hollow so that any of the above-described substances is accommodated or bundled in the space in the particulate carrier. In this case, with the luminescent substance, the particulate case or film needs to be transparent or translucent. With the radioactive substance, the particulate case or film needs to be transparent or translucent with respect to the wavelength band of the electromagnetic waves. The particulate carrier is provided with the labeling element or processed or formed to be identifiable before being introduced and held in the carrier holding portion.

The labeling element may be a bonding substance that specifically reacts with a predetermined luminescent substance or the like that is identifiable through measurement; the bonding substance has not reacted with the luminescent substance yet. An example of such a bonding substance is a receptor that is bondable to a ligand to which the luminescent substance or the like is bonded. The labeling element has potentially been labeled and actualizes the labeling when allowed to react with the predetermined luminescent substance or the like. Consequently, the use of the labeling element allows the particulate carriers to be potentially labeled so as to be mutually identifiable before the particulate carriers are introduced into the carrier holding portion so that the labeling is actualized by reaction after the introduction. This is also included in the labeling prior to the introduction.

Thus, mutually identifying the particulate carriers or the sets of the particulate carriers enables the recognition of the various substances that are or can be immobilized to the particulate carriers, without the need to arrange the particulate carriers so that the particulate carriers are positionally identifiable or to move the particulate carriers in a predetermined order. Therefore, for example, by bringing the particulate carriers into contact with a suspension containing a target substance labeled with a method different from that for the particulate carriers so that the target substance reacts with any of the various substances or bonds to that substance, it is possible to identify the substance to which the target substance has bonded, on the basis of the combination of the labeling of the target substance and the labeling of the particulate carriers.

That is, according to the present invention, even when the particulate carriers are held at arbitrary, free, optional, or irregular positions or in an arbitrary, free, optional, or irregular order, the various substances to which the particulate carriers are or can be immobilized can be recognized without the need to construct an array in which the particulate carriers are arranged at positions associated with any of the various substances or in an order associated with that substance.

A second invention provides the various-substance holder wherein the carrier holding portion includes a tip-like container having an installing opening that can be installed around a nozzle through which gas is sucked and discharged, and a mouth portion through which a fluid is allowed to flow in and out by sucking and discharging the gas.

Here, the "tip-like container" refers to the container having the installing opening to be installed around the nozzle and the mouth portion through which the fluid is allowed to flow in and out. Preferably, the installing opening is formed at an upper end of the tip-like container, while the mouth portion is formed at a lower end of the tip-like container. The tip-like container has a capillary that is preferably formed to be thinner than the installing opening or the nozzle and can be inserted into various containers. The capillary preferably has the mouth portion at a tip thereof. Furthermore, the tip-like container preferably has a storage portion which can store liquid and is in communication with the installing opening and the capillary. This is because the capillary is formed to be thinner than the installing opening and cannot be brought into direct communication with the installing opening. The storage portion preferably has a thick tube formed to be thicker than the capillary. The capillary may be integrated with the storage portion or the thick tube or removably provided. The removable capillary allows the carriers to be easily accommodated in the capillary. The thick tube and the capillary are not limited to the shape of a typical dispensing tip having a larger diameter portion and a smaller diameter portion which is in communication with the larger diameter portion and which corresponds to the capillary. For example, the larger diameter portion may instead be shaped like a quadrangular pyramid, and the smaller diameter portion may instead be a quadrangular prismatic tube. Furthermore, the inner diameter or cross section of the capillary is smaller than the inner diameter of the nozzle to be installed in the installing opening. Moreover, the carriers are accommodated in the capillary. The volume of the capillary is preferably within the range from several microliters to several hundred microliters.

With respect to a material for the tip-like container, at least the capillary portion is preferably composed of a translucent material in order to enable optical measurements. Materials for the tip-like container include, for example, resins such as polyethylene, polypropylene, polystyrene, and acrylic, and glass, metal, and metal compounds. The size of the tip-like container is such that for example, several microliters to several hundred microliters of liquid can be accommodated in the capillary.

The particulate carriers may be accommodated in the capillary in the tip-like container, in the storage portion thereof, or in both the capillary and the storage portion as described below. If the particulate carriers are accommodated in the storage portion, a core that can be inserted into or through the storage portion is provided in the storage portion. A groove or a projection in spiral, zigzag, linear, or serpentine form is further formed on an outer surface of the core so as to form a thin passage between an inner wall of the storage portion and the groove or between the inner wall of the storage portion and the outer surface of the core and the projection so that the particulate carriers can be accommodated along the passage. Alternatively, if the groove or projection with the above-described shape is formed on the inner wall of the storage portion so that a thin passage is formed between the groove and the outer surface of the core or between the inner wall of the storage portion and the projection and the outer surface of the core, the thin passage may be formed by providing the groove or projection with the above-described shape on both the inner wall of the storage portion and the core. This passage has a size such that the particulate carriers are lined up in the passage. These configurations are more compact and rigid than a configuration in which the capillary itself is spirally formed so as to hold the particulate carriers as described below. Furthermore, these passages may be formed in communication with the capillary so as to consecutively hold the particulate carriers in both the storage portion and the capillary.

A third invention provides the various-substance holder wherein the tip-like container has a storage portion which can store liquid and which has the installing opening, and a capillary which is in communication with the storage portion and which has the mouth portion, the capillary being formed to be thinner than the storage portion, and the particulate carriers are held in the capillary.

In this case, holding the particulate carriers in the capillary in a line allows measurements to be more easily performed by scanning the particulate carriers along the capillary. Here, since the particulate carriers are arranged in a line, the diameter of the capillary or a cross section thereof perpendicular to an axial direction needs to have a size or a shape such that the particulate carriers cannot pass each other along the axial direction or at most two particulate carriers can be arranged in a direction perpendicular to the axial direction. That is, the capillary has an inner diameter or width and a length which are larger than the outer diameter of each of the particulate carriers and smaller than the double of the outer diameter.

Then, the particulate carriers can be scanned and measured along the line. These particulate carriers have an outer diameter of, for example, about 0.1 mm to about 3 mm. The capillary has an inner diameter of, for example, about 0.2 mm to about 6 mm.

The capillary need not necessarily be linear but may be curved. For example, the capillary may have a spiral form which turns along a cylinder around an axis joining the mouth portion to the installing opening or which turns convolutedly in a plane. Alternatively, the capillary may be bent or have a U-shaped portion. The capillary may not only have a circular or annular cross section in a direction perpendicular to a flow direction of the fluid but also have for example, a quadrangular inner wall cross section. If the particulate carriers to be held are spherical, the vertexes of the quadrangle serve as grooves through which the fluid can pass.

A fourth invention provides the various-substance holder in which the carrier holding portion has an entrapping portion that entraps the particulate carriers in the carrier holding portion so that the particulate carriers can contact the fluid flowing in from the mouth portion.

Here, an example of the "entrapping portion" has one or more carrier passage inhibiting members provided separately from the holding portion so as to partition the installing opening or to partition the opening from the mouth portion so that the fluid can pass through, while the carriers cannot pass through.

The "carrier passage inhibiting member" is formed using a member different from that forming the tip-like container. The "carrier passage inhibiting member" may be a combination of the wall of the tip-like container or the like and a component obtained by processing the wall of the tip-like container or the like. The carrier passage inhibiting member forms a gap between the carrier passage inhibiting member and the inner wall surface of the container so that the fluid can pass through the gap. However, the through-hole or gap has such a size or shape as prevents each of the particulate carriers from passing through. The carrier passage inhibiting member is, for example, a member provided so as to partition the capillary into a cross, straight lines, radiating lines, a net, or a ring, or a through porous member having a through-hole. The through porous member allows various particulate carriers with a size larger than the pore diameter to be reliably entrapped. The "through porous member" need not be a filter that captures a certain substance by adsorption or the like. However, if the entrapping portion is a filter or a thin-film-like filter such as a membrane, not only the carriers can be prevented from flowing out through the mouth portion or the installing opening but also a predetermined substance can be captured. If the entrapping portion is provided separately from the tip-like container, it is possible to use a member formed like a thin plate or film that is thinner in the flow direction of the fluid or a through porous member having a large pore diameter that still prevents the outflow of the carriers. To prevent the outflow of the particulate carriers both from the mouth portion and from the installing opening, it is preferable to provide the carrier passage inhibiting member in at least two areas so that the particulate carriers are sandwiched between the mouth portion and the installing portion.

Furthermore, providing a separate, removable carrier passage inhibiting member allows the carriers to be easily entrapped and removed.

Additionally, if the tip-like container is processed to form the entrapping portion, pressure required for suction and discharge can be reduced by setting an increased size for the opening portion which still prevents the carriers from flowing out. The entrapping portion composed of the tip-like container itself may have, in order to reduce the thickness of the capillary, a projecting portion that projects in a central direction of the capillary or one or more projecting portions formed by projecting a wall surface of the holding portion in a direction in which the installing portion is partitioned from the mouth portion.

Thus, the tip-like container can be processed and deformed to reliably entrap the particulate carriers without the need to process the particulate carriers.

A fifth invention provides the various-substance holder wherein all or a part of a wall of the carrier holding portion is formed of a conductive member having a predetermined electric resistance value.

In this case, the conductive member provided in the tip-like container can be contacted with a terminal connected to an external power supply circuit to allow current to pass through the conductive member, having the predetermined resistance value. This generates heat. The value of the current is controlled by a control section described below on the basis of the contents of the treatment.

Furthermore, the "predetermined electric resistance value" refers to a value at which the conductive material through which the predetermined current is passed can generate heat required to achieve a temperature that meets the purpose of the treatment. For example, a surface resistance value is, for example, about several hundred .OMEGA. to several .OMEGA. per unit area. A resistance value at which induction heating can be provided is, for example, at least several .OMEGA.cm.

The "conductive member" may be a conductive substance, for example, metal, a metal compound such as metal oxide, alloy, semiconductor, metalloid, or a conductive resin, a combination of any of the conductive substances and a nonconductive substance, for example, ceramics, glass, or a synthetic resin, or a combination of any of the conductive substances. For example, the conductive member may be formed of aluminum, aluminum oxide, tin oxide, iron, an iron alloy, a nichrome alloy, or at least two types of conductive substances bonded together by adhesion, welding, or junction. These members can be inductively heated by passing current through the member, or if the member is formed of iron or an iron alloy, applying a temporally varying magnetic field to the member. If the member is formed by joining two types of conductive substances, the member can be heated or cooled depending on the direction of the current on the basis of a Peltier effect.

The conductive member may be shaped like, for example, a line, a thin film, a foil, a film, a thin plate, a plate, an elongate shape, or a layer. For reinforcement, the conductive member may be bonded or soldered to or deposited on a nonconductive member. The conductive member is controlled to a predetermined temperature by an "electromagnetic signal" (an electric signal or a magnetic signal). A thermodynamic signal based on the application of heat or cool air is not an example of the electromagnetic signal.

The wall has an inner wall surface facing the interior of the tip-like container and an outer wall surface located outside the tip-like container; the portion between the inner wall surface and the outer wall surface corresponds to the integrally formed tip-like container. That is, the wall portion sandwiched between the inner wall surface and outer wall surface of the tip-like container is formed as a solid, indivisible wall made of metal, resin, or the like or a combination of the metal, resin, and the like. Consequently, the conductive member is formed as the whole or a part of the wall, and a conductive member divisible from the wall is thus not an example of the conductive member due to its divisible property: the conductive member is only in contact with the wall, is removably mounted using screws or the like, is removably attached to another member mounted on the wall by welding or the like, or is completely separate from the wall. Thus, by providing the conductive member so that the wall of the tip-like container substantially has a thickness required for the wall of the tip-like container, it is possible to inhibit an increase in the size of the tip-container and in the scale of the whole apparatus to allow the apparatus to be handled without any consciousness of the presence of heating means.

A sixth invention provides the various-substance holder wherein each set of the particulate carriers has at least two separate particulate carriers, at least one of the at least two separate particulate carriers is a reacting particle to which the chemical substance is or can be immobilized, and at least one of the at least two separate particulate carriers which is different from the particulate carrier to which the chemical substance is or can be immobilized is a labeling particle labeled so as to allow type of the chemical substance or the set of the particulate carriers to be identified.

Here, the appropriate "reacting particle" is, for example, a raw material having surface activity or to which the chemical substance (reactive substance) can be sufficiently immobilized or any material which has the property of allowing the chemical substance to be immobilized to the material, as described for the particulate carriers. On the other hand, the appropriate "labeling particle" is a raw material coated with a fluorescent substance, a chemiluminescent substance, or a radioactive substance or with any of various pigments, or a particle having an identifiable predetermined shape, for example, a cube, a cylinder, a prism, a cone, or a cross, or an identifiable predetermined size, or a substance having a combination of some or all of the fluorescent substance, chemiluminescent substance, radioactive substance, and predetermined shape. The labeling particle preferably has the property of minimizing the adhesion of the various substances or substances that are bondable to the various substances.

A seventh invention provides the various-substance holder wherein each set of the particulate carriers has at least two separate particulate carriers, and at least one of the at least two separate particulate carriers is a boundary particle which eliminates an effect of the labeling between the sets of the particulate carriers or which defines a boundary between the sets of the particulate carriers.

Here, the reacting particle itself may be labeled, or the reacting particle may be labeled after reaction on the basis of a second label described below. If a particle different from the reacting particle is labeled, at least three particulate carriers, the reacting particle, labeling particle, and boundary particle, may belong to each set, or the labeling particle itself may be the boundary particle and at least two particles may belong to each set. An example of the "boundary particle" is a particle formed of metal, ceramics, or the like which blocks light such as fluorescence or chemiluminescence.

An eighth invention provides the various-substance holder wherein one or more protrusions or one or more projections or grooves are formed on one of an outer surface of the particulate carrier and an inner wall of a part of the carrier holding portion which holds the particulate carrier.

Here, the expression "part of the carrier holding portion which holds the particulate carrier" refers to, for example, the capillary portion in which the particulate carriers are held in a line. Thus, even if the particulate carriers are spherical and the capillary has a cylindrical inner wall or the entrapping portion has a circular through hole, the particulate carriers are prevented from adhering to the inner wall of the carrier holding portion or closing the through-hole to block the flow of the fluid.

A ninth invention provides the various-substance holder wherein a space in the carrier holding portion holding the particulate carriers which space can accommodate a fluid has a volume of about several microliters to several hundred microliters.

Here, the "space which can accommodate the fluid" is generally a space formed between the surface of the carriers entrapped in the capillary and the inner wall surface of the capillary.

When the volume of the capillary is thus limited, even if a very small amount of liquid, that is, several microliters to several hundred microliters of liquid, is sucked into the capillary, the liquid can be uniformly or evenly contacted with the surface of the carriers. In the field of biochemistry, particularly DNA, the liquid of this very small amount can normally be easily extracted from a living organism and handled. Furthermore, in addition to the capillary, the tip-like container has a thick tube which is in communication with the capillary and which has a volume several to several tens of times as large as that of the capillary. This allows various liquid amounts to be handled.

A tenth invention provides a various-substance holder treating apparatus comprising a nozzle head having one or more nozzles through which gas is sucked and discharged, a suction and discharge mechanism that sucks and discharges the gas via the nozzle, and, one or more various-substance holders each having a plurality of particulate carriers or plural sets of the particulate carriers to which plural types of chemical substances are or can be immobilized and a carrier holding portion holding the plurality of particulate carriers or the plural sets of particulate carriers in a substantially stationary state such that the plurality of particulate carriers or the plural sets of the particulate carriers can be externally measured and being or capable of being installed in the nozzle, wherein each of the plurality of particulate carriers or at least one of the particulate carriers belonging to the plural sets of the particulate carriers are labeled according to types of the chemical substances or for each of the particulate carriers or each set of the particulate carriers so as to be mutually identifiable before the particulate carriers are introduced and held in the carrier holding portion.

Here, the "various-substance holder" is according to any of the first to ninth inventions. In particular, the various-substance holder needs to be or to be able to be installed on the nozzle.

An eleventh invention provides the various-substance holder treating apparatus comprising a liquid accommodating portion group that accommodates or can accommodate various liquids, moving means for moving the nozzle head relative to the liquid accommodating portion group, and a control section that controls amount, speed, count, time, or positions of suction and discharge performed by the nozzle on the basis of substance conditions including a structure of the various-substance holder, types and concentrations of various substances which are immobilized to the particulate carriers or which are present in the fluid, amount of the liquid, and coordinate positions including a position where the liquid is accommodated, as well as a content of a treatment.

Here, the "content of the treatment" refers to, for example, reaction, cleaning, transfer, dispensation, separation, extraction, heating, cooling, purification, measurement, mixture, dissociation, elution, or agitation, or any of these treatments combined into a sequence according to the purpose of the treatments and a predetermined order or a predetermined time schedule with duplication of the treatments admitted. The "time" includes the durations and timings of the suction and discharge. Setting the durations or timings enables intermittent, continuous, and discontinuous suction and discharge to be set.

In the "reaction" treatment, for example, control is performed such that according to the substance conditions, the suction and discharge determined on the basis of the substance conditions described above are repeated at the position of the container that accommodates the appropriate reagent, at a predetermined speed and at a liquid level that is equal to, for example, 80 percents of the volume of the carrier entrapping area in the capillary. For the control, the suction and discharge counts are specified according to the substance conditions. In the "cleaning" treatment, for example, control is performed such that according to the substance conditions, the suction and discharge are repeated a predetermined number of times at the position of the container that accommodates a cleaning fluid, at a predetermined speed determined on the basis of the treatment. Similarly, the suction and discharge are controlled according to the above-described treatments. For the "speed", if for example, DNA is to be handled, since the size of DNA is smaller than that of protein, the speed needs to be increased in order to increase the likelihood that DNAs encounter each other. Furthermore, the speed varies depending on the content of the treatment. The suction and discharge speeds are lower for the cleaning and agitation than for the reaction treatment.

The "structure of the various-substance holder" includes the shape of the tip, the positions of the entrapped particulate carriers, the shape and properties of the accommodated particulate carriers, or the shape of the entrapping portion. The specification of the suction and discharge operations according to the "types of the chemical substances" means that for example, if the size of the substance is smaller than that of protein as is the case with a genetic substance such as DNA, the substance is easier to handle at a lower liquid level and an a higher speed. This is because the likelihood that DNAs encounter each other generally decreases consistently with the size thereof.

Here, the various-substance holder comprises, for example, a tip-like container having an installing opening installed around the nozzle, a mouth portion through which a fluid is allowed to flow in and out by sucking and discharging the gas, and a capillary that is thinner than the nozzle, and an entrapping portion formed in the tip-like container to entrap the carriers in the holder so that a predetermined biological substance which is or can be immobilized to a plurality of externally identifiable, predetermined different particulate carriers and which is sized or shaped to be passable through the mouth portion can contact a fluid flowing into the holder.

A twelfth invention provides the various-substance holder treating apparatus comprising a receiving device that receives signals from the particulate carriers held by the carrier holding portion and an analyzing device that performs analysis on the basis of the signals from the receiving device.

Here, the "reception of the signals" includes the reception of electromagnetic wave signals of various bands, including the reception of optical signals. The receiving device receives signals, at a time, from a plurality of particulate carrier holders installed in the nozzle head having the plurality of nozzles or sequentially receives light from each of the various-substance holders. In the latter case, the moving means for making relative movement between the receiving device and the container is used to sequentially and relatively convey the tips or the receiving devices one by one. In this case, measurements are made at different points in time. Thus, when a certain reagent, for example, DNA, is to be extracted, a PCR reactant for a PCR pretreatment needs to be dispensed or a matrix solution for chemiluminescence needs to be poured, immediately before or a specified time before the reaction. Therefore, instead of dispensing all of the solution at a time, it is preferable to dispense specified amounts of solution at different points in time. If fluorescence is measured, a light emitting device that emits predetermined excitation light is provided in the container.

A thirteenth invention provides the various-substance holder treating apparatus wherein the analyzing device performs analysis on the basis of signals which are received by the receiving device and based on a first label that enables the particulate carriers to be mutually identified according to the types of the chemical substances or for each particulate carrier or each set of the particulate carriers before the particulate carriers are introduced and held in the carrier holding portion, and signals that are received by the receiving device and based on a second label that labels the introduced and held particulate carriers.

Here, the "signals based on the first label" need to indicate that the signals belong to the first label and need to be identifiable from one another. The "signals based on the second label" need to indicate that the signals belong to the second label and need to be identifiable from one another. Consequently, the "signals based on the first label" need to be identifiable from the "signals based on the second label". Furthermore, the amount of reaction with the various substances can be measured on the basis of the intensity of the signals based on the second label or the amount of signals received.

A fourteenth invention provides the various-substance holder treating apparatus comprising a temperature increasing and reducing member which is provided outside the carrier holding portion close to or in contact with the carrier holding portion or which is provided outside the carrier holding portion such that the member can be placed close to or in contact with the carrier holding portion, the temperature increasing and reducing member increasing or reducing temperature in response to an external signal.

Here, the "temperature increasing and reducing member" refers to a member or device that is able to increase or reduce the temperature thereof in response to the external signal. The "signal" refers to an electromagnetic signal, that is, an electric or magnetic signal, when the temperature increasing and reducing member is a conductive member. It is possible to detect the temperature of the temperature increasing and reducing member to generate a signal on the basis of the temperature.

The temperature increasing and reducing member is preferably provided so as to be movable relative to the variable-substance holder. Furthermore, in this case, the control section controls not only the suction and discharge but also the temperature on the basis of the content of the treatment.

A fifteenth invention provides the various-substance holder treating apparatus wherein the nozzle head has a plurality of batch nozzles and one separate nozzle arranged in a column direction, and the suction and discharge mechanism allows gas to be sucked into and discharged from the batch nozzles and separate nozzle in the nozzle head at a time, and wherein the moving means has nozzle head moving means for moving the nozzle head along a row direction relative to a stage having the liquid accommodating portion group, and a row and column path conveying means having a conveyance path including a column conveyance path located on a moving path of the batch nozzles and extending along the column direction and a row conveyance path located on a moving path of the separate nozzle and extending along the row direction, the row and column path conveying means conveying, along the conveyance path, a conveying and accommodating portion capable of accommodating the tip-like containers removed from the batch nozzles or a liquid discharged from the batch nozzle head.

Here, the "row direction" and the "column direction need not necessarily cross at right angles like an X direction (horizontal direction) and a Y direction (vertical direction) but may cross obliquely. The "batch nozzle head" and the "separate nozzle head" may be independently movable. Furthermore, the row and column path conveying means may have, for example, a closed conveyance path shaped like a quadrangle, a polygon, or the like or an open conveyance path provided that the row and column path conveying means has the row conveyance path and column conveyance path provided on the moving path of the nozzle head.

Here, the "conveying and accommodating portion" is a portion of the conveying means which accommodates the tip or liquid. The number of conveying and accommodating portions is preferably the same as that of the nozzles in the batch nozzle head.

A sixteenth invention provides the various-substance holder treating apparatus comprising receiving means for receiving a signal from the removed tip-like container or the conveying and accommodating portion, the receiving means being provided at a predetermined position along the conveyance path of the row and column path conveying means.

A seventeenth invention provides a various-substance holder manufacturing device comprising a carrier capturing portion capable of capturing a plurality of particulate carriers or particulate carriers belonging to plural sets of the particulate carriers to which plural types of chemical substances are or can be immobilized, each of the plurality of particulate carriers or at least one of the particulate carriers belonging to the plural sets of the particulate carriers being labeled according to types of the chemical substances or for each of the particulate carriers or for each set of the particulate carriers, and a carrier capturing and moving portion that moves the particulate carriers captured by the carrier capturing portion together with the carrier capturing portion, wherein in order to manufacture a various-substance holder, the particulate carriers captured by the carrier capturing portion are moved to a carrier holding portion which can hold the plurality of particulate carriers or the plural sets of particulate carriers, the carrier holding portion holding the particulate carriers in a substantially stationary state such that the particulate carriers can be externally measured.

Here, the "carrier capturing transferring portion" may have, for example, a sucking portion capable of sucking gas, a tubular member capable of capturing the particulate carriers through the suction by the sucking portion, and a tubular member moving means capable of moving the tubular member relative to the carrier holding portion according to any of the first invention to the ninth invention. For example, the tubular member uses a tip thereof to capture the particulate carriers one by one.

An eighteenth invention provides the various-substance holder manufacturing device wherein the carrier holding portion is a tip-like container and has an installing opening that can be installed around a nozzle through which gas is sucked and discharged and a mouth portion through which a fluid is allowed to flow in and out by sucking and discharging the gas, and the apparatus comprises a tip-like container support portion that supports the tip-like container so that the installing opening or the mouth portion faces upward, an upward-broadening funnel-like guide surrounding a periphery of the upward-facing installing opening or mouth portion in the supported tip-like container and a lower sucking mechanism that sucks gas into the downward-facing mouth portion or installing opening in the tip-like container.

A nineteenth invention provides the various-substance holder manufacturing device comprising a carrier accommodating portion group that accommodates or can accommodate various particulate carriers, and a carrier holding portion accommodating portion that accommodate the carrier holding portions.

A twentieth invention provides a various-substance holder manufacturing method comprising an immobilizing and labeling step of immobilizing plural types of chemical substances to a plurality of the particulate carriers or labeling particulate carriers to which the chemical substances are immobilized, a plurality of particulate carriers to which the chemical substances can be immobilized, or particulate carriers other than the particulate carriers to which the chemical substances are or can be immobilized, according to types of the chemical substances or for each of the particulate carriers or for each set of the particulate carriers including the above-described particulate carriers, so that the particulate carriers are mutually identifiable, and an introducing and holding step of introducing and holding the plurality of particulate carriers or the plural sets of the particulate carriers in the carrier holding portion in a substantially stationary state such that the particulate carriers can be externally measured.

A twenty-first invention provides the various-substance holder manufacturing method wherein the introducing and holding step comprises, an introducing step of transferring and introducing, into the carrier holding portion, the plurality of particulate carriers or the plural sets of the particulate carriers to which the chemical substances are or can be immobilized and which are labeled so as to be mutually identifiable, and a holding step of entrapping and holding the plurality of particulate carriers or the plural sets of the particulate carriers introduced into the carrier holding portion, in the carrier holding portion in the substantially stationary state.

Here, the introducing and holding step is executed by using, for example, a tubular member to hold the particulate carriers at a tip thereof and transferring the particulate carriers to the carrier holding portion; the tubular portion is in communication with a sucking portion that sucks gas from a particulate carrier accommodating portion located on a stage and accommodating the particulate carriers.

A twenty-second invention provides a various-substance holder treating method comprising an installing step of installing one or more various-substance holders in one or more nozzles through which gas is sucked and discharged, the one or more various-substance holders comprising one or more carrier holding portions each having an installing opening that can be installed around each of the nozzles and a mouth portion through which a fluid is allowed to flow in and out by sucking and discharging the gas, each of the carrier holding portions internally holding a plurality of particulate carriers or plural sets of particulate carriers to which plural types of chemical substances are or can be immobilized, in a substantially stationary state such that the particulate carriers can be externally measured, each of the plurality of particulate carriers or at least one of the particulate carriers belonging to the plural sets of the particulate carriers being labeled according to types of the chemical substances or for each of the particulate carriers or each set of the particulate carriers so as to be mutually identifiable, before the particulate carriers are introduced and held in the carrier holding portion, a reaction step of relatively moving the nozzles to sequentially move the mouth portions of the various-substance holders to one or more predetermined liquid accommodating portions to contact the particulate carriers with a liquid in the liquid accommodating portions for reaction, and an analyzing step of performing analysis on the basis of received signals from the particulate carriers held in the carrier holding portions.

Here, the carrier holding portion having the installing opening that can be installed around the nozzle and the mouth portion through which the fluid is allowed to flow in and out by sucking and discharging the gas is a tip-like container.

A twenty-third invention provides the various-substance holder treating method wherein the analyzing step performs analysis on the basis of signals which are received in the receiving step and based on a first label that enables the particulate carriers to be mutually identified according to the types of the chemical substances or for each particulate carrier or each set of the particulate carriers before the particulate carriers are introduced and held in the carrier, and signals that are received in the receiving step and based on a second label that labels the introduced and held particulate carriers.

If the first label involves, for example, a fluorescent substance and the second label involves a chemiluminescent substance, the signals based on the first label are received by irradiating the particulate carriers with excitation light. After the reaction step, reception of the signals based on the first and second labels during a single scan can be achieved by, for example, repeatedly turning on and off an excitation light pulse in accordance with the labeling of the particulate carriers.

A twenty-fourth invention provides the various-substance holder treating method wherein the reaction step moves the nozzle with the various-substance holder installed therein to a predetermined liquid accommodating portion, and controls an operation of suction and discharge comprising amounts, speeds, counts, time, and positions of the suction and discharge via the nozzle on the basis of substance conditions including a structure of the carrier holding portion, types or concentrations of the chemical substances which are immobilized to the particulate carriers or which are present in the liquid, amount of the liquid, or coordinates of positions including a position where the liquid is accommodated, and a content of a treatment, to contact the chemical substance immobilized to the particulate carriers with the liquid accommodated in the liquid accommodating portion for reaction.

A twenty-fifth invention provides the various-substance holder treating method comprising a receiving step of, after the reaction step, receiving the signals from the particulate carriers accommodated in the carrier holding portion.

The signals based on the first label are irrelevant to the reaction and may thus be received before the receiving step. The signals based on the second label are received after the reaction step. Thus, in this case, scanning along the particulate carriers is performed at least twice. On the other hand, if the reception is performed on the basis of the signals based on the first and second labels after the reaction step, only a single scanning operation is required.

A twenty-sixth invention provides the various-substance holder treating method wherein the reaction step comprises a temperature increasing and reducing step of increasing or reducing a temperature in the carrier holding portion.

According to the first or twentieth invention, the particulate carriers or the sets of particulate carriers are labeled so as to be mutually identifiable according to the types of the various substances (plural types of chemical substances) or for each of the particulate carriers or each set of the particulate carriers before the particulate carriers are introduced and held in the carrier holding portion. Thus, when the particulate carriers are introduced and held, it is unnecessary to form an array in which the particulate carriers are arranged at predetermined positions according to the various substances in order to mutually identify the various substances. The particulate carriers have only to be held in a substantially stationary state at arbitrary or optional positions unassociated with the various substances or in an arbitrary or optional order. This eliminates the need for time and effort to arrange the various substances, allowing the particulate carriers to be easily and quickly introduced and held.

Furthermore, according to the present invention, the various substances held by the particulate carriers are not identified on the basis of the positions associated with the particulate carriers. This eliminates the need to immobilize the particulate carriers at the exact positions or maintain the exact order of the particulate carriers for precise measurements. Additionally, the particulate carriers are held in the substantially stationary state instead of being migrated by application of a fluid force. This allows the particulate carriers to be easily handled and measured by simple control instead of complicated synchronous control or the like, and increases accuracy.

Moreover, according to the present invention, the same particulate carriers are consistently used for immobilization, reaction, measurement, and the like of the various substances. The present invention is thus suitable for consistent, automatic performance of a series of treatments.

According to the present invention, the plurality of particulate carriers to which the various substances are or can be immobilized can be easily introduced and held in the carrier holding portion, holding the particulate carriers, without the need to pre-specify the positions or order of the particulate carriers. Consequently, the treatments of the particulate carriers themselves such as the immobilization thereof can be easily performed in an area different from that in which the carrier holding portion is located. This makes it possible to increase the efficiency, reliability and credibility of the treatments.

According to the present invention, the plurality of particulate carriers to which the various substances are or can be immobilized are labeled before holding. The particulate carriers are held at any positions in the substantially stationary state for measurements. Thus, the present invention requires only the determination of the presence of a labeling substance and eliminates the need to precisely measure positional coordinates. This facilitates measurements.

Moreover, according to the present invention, each set of particulate carriers including a plurality of particulate carriers can be labeled. Consequently, by classifying the particulate carriers belonging to the set of particulate carriers into those to which the various substances are or can be immobilized and those used for labeling, it is possible to assign the different functions to the respective particulate carriers. Therefore, the functions such as labeling and immobilization can be specialized for the respective particulate carriers. This enables precise treatments.

Furthermore, various labeling operations can be performed by freely setting the number of particulate carriers belonging to each set of particulate carriers. The present invention is thus expandable and can exhibit diversity and flexibility.

According to the second invention, the tip-like container allows the carrier holding portion to be installed in the nozzle through which gas is sucked and discharged. Consequently, the nozzle is used to control the amount, speed, position, count, timing, and the like of the suction and discharge of a fluid to enable the consistently automatic performance of a series of treatments including the immobilization, transfer, reaction, and measurement of the various substances.

According to the third invention, the tip-like container is formed to have the storage portion with the installing opening and the capillary formed to be thinner than the storage portion. Thus, for example, the particulate carriers are held in the capillary, for example, in a line so as to be one-dimensionally held therein. This enables the particulate carriers to be reliably measured. Furthermore, the particulate carriers can be easily measured by performing measurements such that the particulate carriers are scanned along the capillary.

Moreover, introducing and discharging the fluid along the capillary enables reliable contact with the fluid. Furthermore, the capillary is convenient for sucking and discharging of the fluid because the capillary can be inserted into various external containers. Additionally, according to the present invention, during the treatments, the particulate carriers are always contactable with the fluid. The treatments can thus be efficiently performed.

According to the fourth invention, the entrapping portion is provided to allow the particulate carriers to be reliably entrapped in the carrier holding portion so that the particulate carriers are contactable with the fluid. This allows the particulate carriers held in the carrier holding portion so as not to flow out to be contacted with the fluid, while preventing the presence of the particulate carriers from blocking the flow of the fluid.

According to the fifth invention, reaction temperature can be controlled by passing current through the conductive member formed on the entire wall of or on a part of the wall of the carrier holding portion to cause the conductive member to generate heat to heat or cool the particulate carriers and fluid accommodated in the carrier holding portion.

Consequently, compared to the case in which heating means such as a heater is provided outside the wall of the carrier holding portion, the present invention keeps the conductive member in direct contact with the tip-like container, preventing the wall from reflecting heat. Heat can thus be more efficiently transferred to the interior of the tip-like container. The present invention thus offers a high heat efficiently, enabling accurate temperature control.

Moreover, the wall of the carrier holding portion formed of the conductive member improves the heat efficiency and eliminates the need to provide, outside the tip-like container, heating means such as a metal block which is larger than required. Only a driving device for the conductive member needs to be provided outside. Consequently, the external structure can be simplified to enable a reduction in the scale of the whole apparatus.

The optimum temperature increasing and reducing member can be pre-provided in the carrier holding portion. This eliminates the need to provide heating means that meet various conditions, allowing the present invention to be used for diverse general purposes.

Since the conductive member is in direct contact with the carrier holding portion, the temperature of the liquid can be accurately controlled so as to obtain faithful responses.

The present invention can reduce the amount of time from provision of a signal for liquid heating or cooling to the carrier holding portion and the conductive member until the distribution of temperature indicates a uniform liquid temperature. The treatments can thus be quickly and efficiently performed.

According to the sixth invention, each set of the particulate carriers having the at least two separate particulate carriers has the at least one particulate carrier to which any of the various substances is or can be immobilized and the at least one particulate carrier that identifiably labels the substance or the set. This makes it possible to separately use the particulate carrier having the function of allowing any of the various substances to be immobilized and the particulate carrier that performs a labeling operation. The different types of particulate carriers suitable for the respective purposes can be used to very reliably immobilize and label the substance. Furthermore, since the plurality of particulate carriers can be combined for the labeling, a large number of various substances or the like can be identified using a few types of labeled particulate carriers.

According to a seventh invention, each set of the particulate carriers having the at least two separate particulate carriers has the at least one particulate carrier for labeling and the boundary particle which eliminates the effect between the sets of the particulate carriers or which defines the boundary between the sets of the particulate carriers. Consequently, labeling can be reliably performed for each set, improving reliability. In particular, if labeling is performed so that the particulate carriers are arranged in a line and so that the sets of the particulate carriers have different luminescence intensities, reliable measurements of the possible effect between the adjacent sets can be achieved by using the light-blocking boundary particle between the adjacent sets of the particulate carriers.

According to the eighth invention, the gap is formed between the outer surface of the particulate carriers and the inner wall of the carrier holding portion, which holds the particulate carriers. This prevents the particulate carriers from impeding the flow of the fluid, allowing the introduced fluid to reliably contact the particulate carriers. In particular, a protruding portion is provided on the outer surface of at least one of the plurality of particulate carriers held in the capillary which is located at one end thereof. Then, even when the entrapping portion has a circular through-hole, the particulate carrier is prevented from closing the through-hole to block the flow of the fluid. This ensures the reliable contact between the particulate carriers and the fluid.

According to the ninth invention, in the part (for example, the capillary) of the carrier holding portion which holds the particulate carriers, the space between the surface of the particulate carriers held in the carrier holding portion and the inner wall surface of the carrier holding portion has a volume limited to the amount (very small amount) of the liquid for the treatments. This enables the liquid sucked into the carrier holding portion to be contacted with the entire surface of the particulate carriers. Consequently, the very small amount of liquid can be reliably handled.

According to the tenth or twenty-second invention, each various-substance holder is installed on the movable nozzle. Thus, the liquid can be introduced into the carrier holding portion, which can subsequently discharge the liquid. This allows the treatments of the various-substance holder to be consistently achieved. Furthermore, the apparatus enables a plurality of the nozzles to be used in union, allowing concurrent, batch treatments to be efficiently performed. Furthermore, the treatments of various-substance holder can be consistently automated.

According to the eleventh invention, the carrier holding portion of the various-substance holder holding the particulate carriers to which the various substances are or can be immobilized is installed on the nozzle. Then, the amounts, speeds, counts, or positions of the suction and discharge through the nozzle is controlled on the basis of the substance conditions including the shape of the carrier holding portion, the shape and size of the particulate carriers, the type of any of the various substances immobilized to or suspended in the particulate carriers, the amount of the liquid, and the coordinate positions including the position where the liquid is accommodated, as well as the treatment conditions including incubation time, temperature, or the content of the treatment.

Thus, the present invention uses the various-substance holder having the predetermined structure and precisely controls the suction and discharge. This makes it possible to easily, consistently, reliably, quickly, and efficiently perform the treatments such as reaction, agitation, and cleaning on the various substances that are or can be immobilized to the particulate carriers entrapped in the carrier holding portion of the various-substance holder. Furthermore, the present invention makes it possible to deal with various treatments by varying the contents of the control. The present invention can thus exhibit diversity and flexibility.

According to the twelfth or twenty-fifth invention, the signals from the particulate carriers are received to allow the treatment ending with the measurement to be performed consistently, reliably, quickly, and efficiently.

According to the thirteenth or twenty-third invention, the analysis is performed on the basis of the combination of the signal based on the first label that allows the type of each of the various substances to be identified and the signal based on the second label that labels the introduced and held particulate carriers. The analysis can thus be performed by detecting label signal information of the same level without the need to extract positional information. The analysis is therefore easy.

According to the fourteenth or twenty-sixth invention, the temperature of the carrier holding portion of the various-substance holder, thus the temperature of the particulate carriers held in the carrier holding portion, is controlled by moving the external temperature increasing and reducing member close to the particulate carriers. Consequently, the present invention allows reaction to occur more efficiently and reliably than the case where a container provided outside the various-substance holder is heated to control the temperature of the liquid to cause the reaction.

According to the fifteenth invention, the batch nozzle and the separate nozzle can be concurrently moved in the row direction. The row and column path conveying means having the conveyance path with the column conveyance path and the row conveyance path is provided on the moving path of the batch nozzle and the separate nozzle. Consequently, the conveying means allows the treatments to be performed using either the batch nozzle or the separate nozzle. The simple, compact structure using the small number of nozzles enables diverse, complicated treatments to be achieved without the need for a large number of nozzles or a matrix arrangement of suction and discharge mechanisms.

Furthermore, when a large number of treatment targets are subjected to a suction and discharge treatment, common treatment items are batch-treated using the batch nozzle, whereas treatment items that need to be individually treated are individually treated using the separate nozzle. The diverse treatments can be efficiently and quickly performed.

In particular, the present invention is suitable for the case where individual measurements are to be performed and a required reagent is added immediately before the measurement or where a reagent that needs to be maintained at a predetermined temperature is added immediately before the individual treatment.

According to the sixteenth invention, the light receiving means is provided in at least one area on the conveyance path of the row and column path conveying means. In the treatment corresponding to the each of the plurality of nozzles for the treatments, measurements can be sequentially performed using a small number of the receiving means. Consequently, the apparatus can be simplified. In particular, reagents required only immediately before light reception by the light receiving means can be sequentially loaded immediately before the light reception. The light reception can thus be efficiently and reliably achieved.

According to the seventeenth invention, the particulate carriers are individually captured by suction or the like and can thus be taken out of the container and transferred and introduced into the carrier holding portion. Consequently, the particulate carriers can be handled in the air without being suspended in the liquid. The various-substance holder can thus be easily manufactured.

According to the eighteenth invention, the particulate carriers can be reliably introduced and held in the carrier holding portion without being suspended in the liquid. The various-substance holder can thus be easily and reliably manufactured.

According to the nineteenth invention, the various-substance holder has the carrier holding portion accommodating portion that accommodates the carrier holding portion on the stage. This makes it possible to automate an entire process from the introduction of the particulate carriers into the carrier holding portion to the installation of the carrier holding portion on the nozzle instead of manually executing the process.

According to the twenty-first invention, the various-substance holder can be manufactured by transferring the plurality of particulate carriers to which the various substances are or can be immobilized, to the position of the carrier holding portion. This operation is performed regardless of the order of transfer of the particulate carriers or the sets of the particulate carriers or the positions of the particulate carriers in the carrier holding portion. The various-substance holder can thus be easily manufactured.

According to the twenty-fourth invention, the various-substance holder with the particulate carriers entrapped in the tip-like container, corresponding to the carrier holding portion, is installed on the nozzle; the various substances are or can be immobilized to the particulate carriers. The amounts, speeds, counts, or positions of the suction and discharge through the nozzle is controlled on the basis of the substance conditions including the type of any of the various substances immobilized to or suspended in the particulate carriers, the amount of the liquid, and the coordinate positions including the position where the liquid is accommodated, as well as the treatment conditions including the incubation time, temperature, or the content of the treatment. Therefore, the present invention uses the various-substance holder having the predetermined structure and precisely controls the suction and discharge. This makes it possible to easily, consistently, reliably, quickly, and efficiently perform the treatments on the various substances that are or can be immobilized to the particulate carriers entrapped in the carrier holding portion, for example, reaction of the substance with the sucked liquid, agitation of the liquid, and cleaning of the substance. Furthermore, the present invention makes it possible to deal with various treatments by varying the contents of the control. The present invention can thus exhibit diversity and flexibility.

DESCRIPTION OF SYMBOLS

Figure 1:
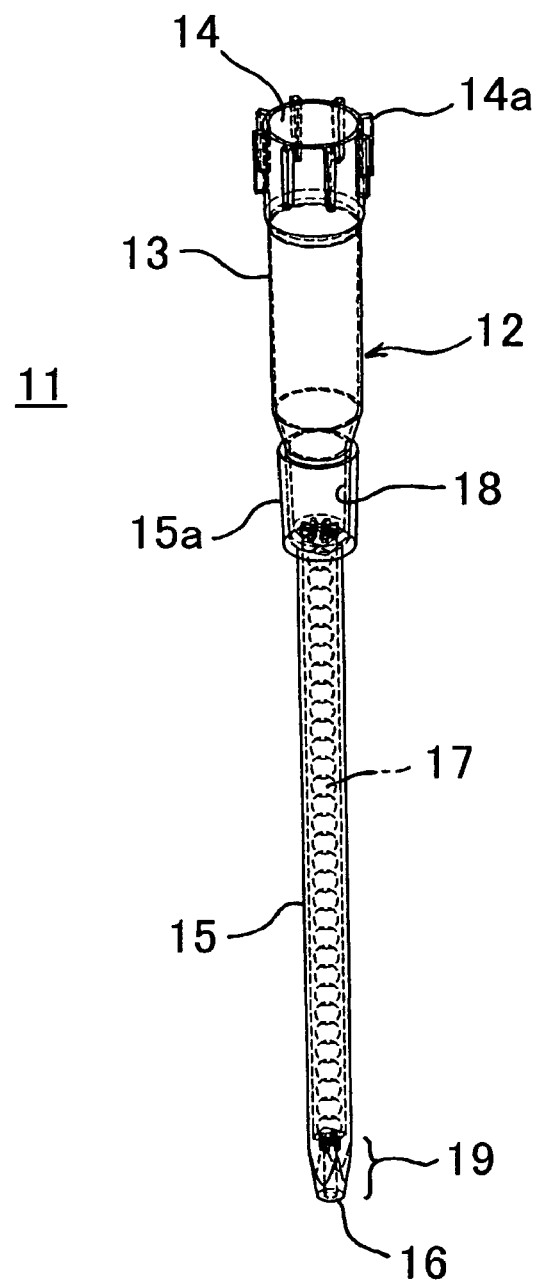
FIG. 1 is a perspective view of a various-substance holder according to a first embodiment.

10 Various-substance holder treating apparatus
11, 30, 41, 50, 52, 58, 63, 65, 66 Various-substance holders
12, 24, 31, 42, 53, 59, 67 Tip-like containers
13, 32, 43, 54, 68 Thick tubes
15, 25, 34, 45, 55, 60, 69 Capillaries
17 Particles (particulate carriers)
61, 61a, 611a Particle aggregates (sets of particulate carriers)
84 Nozzle head
103 Conveyor (row and column path conveying means)
106 Light receiving portion

BEST MODE FOR CARRYING OUT THE INVENTION

The prevent invention labels particulate carriers or sets of the particulate carriers so that the particulate carriers are mutually identifiable before the particulate carriers are introduced into a carrier holding portion. The present invention has thus improved the efficiency of treatments. Furthermore, the particulate carriers introduced into the carrier holding portion are held in a substantially stationary state so as to be externally measurable. The present invention has thus realized a consistently automated treatment from sufficient reaction with various substances to measurements.

Now, embodiments of the present invention will be described with reference to the drawings. The description of the embodiments should not be interpreted to limit the present invention unless otherwise specified.

FIG. 1 shows a perspective view of a various-substance holder 11 according to a first embodiment of the present invention. The various-substance holder 11 has a tip-like container 12 which is translucent and which serves as a carrier holding portion; the tip-like container has a thick tube 13 as a storage portion that can store a liquid and a capillary 15 formed to be thinner than the thick tube 13. The thick tube 13 has an installing opening 14 formed at an upper end thereof and which is to be installed around a nozzle (not shown) used to suck and discharge gas. The capillary 15 has a mouth portion 16 formed at a leading end thereof and through which a fluid is allowed to flow in and out by sucking and discharging the gas.

A plurality of (in this case, 31) mutually identifiably labeled particles 17 of the same shape (for example, sphere) and the same size are held in the capillary 15 in a line along the axial direction of the capillary 15 in a substantially stationary state such that the particles are externally individually measurable; one of plural types of biological substances as chemical substances (various substances) are or can be immobilized to the particles 17. Before introduced into the tip-like container 12, the particles 17 are labeled with a luminescent substance such as a fluorescent substance or a chemiluminescent substance so as to be mutually identifiable for each of the biological substances as the various substances which are or can be immobilized to the particles 17.

A thick tube portion including the thick tube 13 and a capillary portion including the capillary 15 are removably provided. The thick tube portion is formed to have a diameter slightly smaller than that of the thick tube 13, at a lower end 18 thereof which is opposite the installing opening 14. The capillary portion includes a fitting portion 15a formed at the top of the capillary 15 and having a diameter slightly larger than that of the capillary 15. The lower end 18 can be fitted into the fitting portion 15a. The lower end 18 is thus fitted into the fitting portion 15a to combine the thick tube portion with the capillary portion.

The capillary 15 has a tapered leading end portion 19 formed at a lower part of the capillary and having the mouth portion 16 at a leading end of the leading end portion, to prevent the particles 17 from flowing out through the mouth portion 16.

Figure 2:
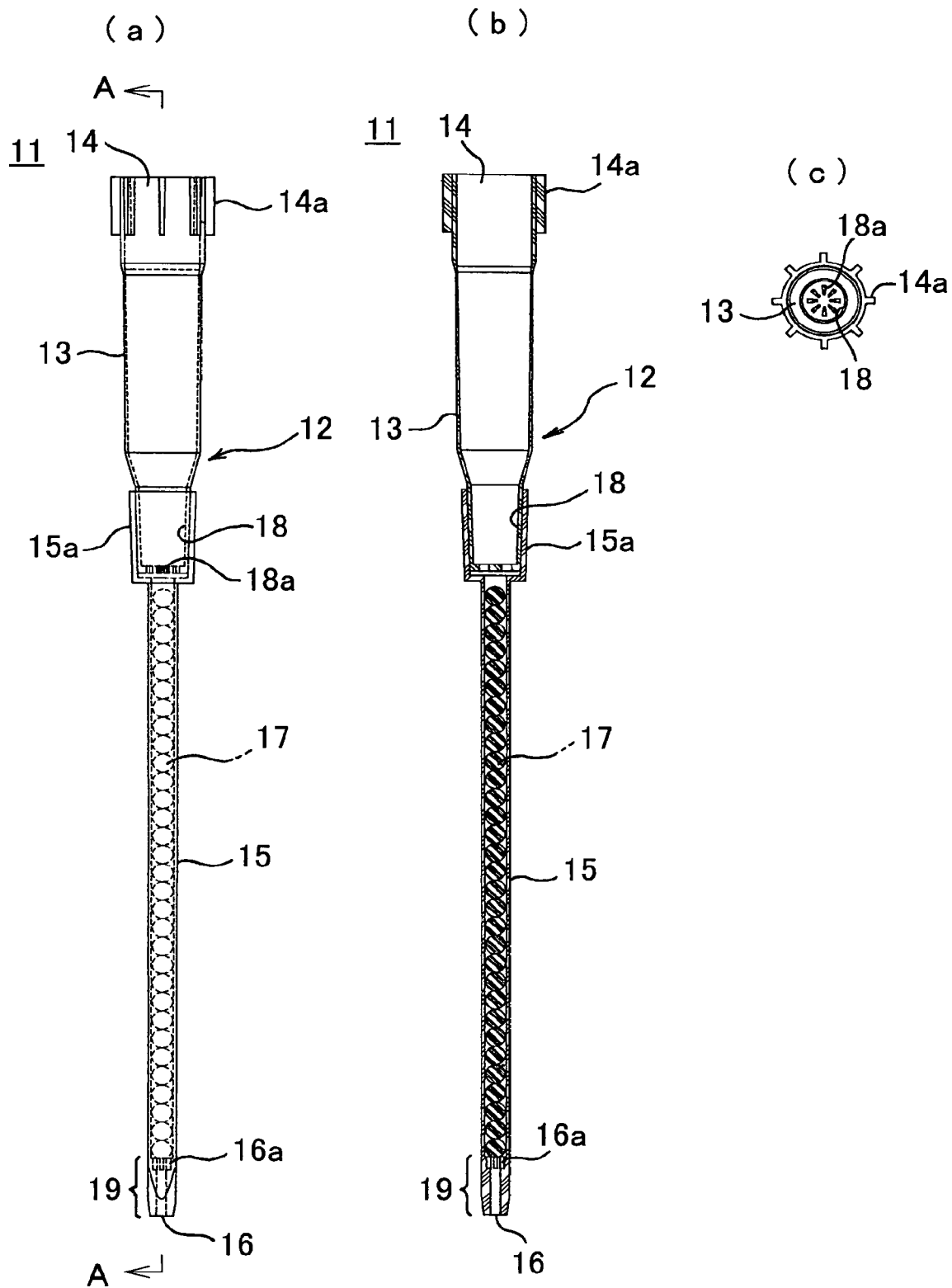
FIG. 2(a) is a front view of the various-substance holder according to the first embodiment.
FIG. 2(b) is a sectional view of the various-substance holder according to the first embodiment.
FIG. 2(c) is a plan view of the various-substance holder according to the first Embodiment.

FIG. 2(a) is an enlarged front view showing the various-substance holder 11 in detail. FIG. 2(b) is a sectional view of the various-substance holder 11 as viewed in the direction of line AA in FIG. 2(a). FIG. 2(c) is a plan view of the various-substance holder.

As shown in FIGS. 2(a), 2(b), and 2(c), radial openings 18a each having a width or length smaller than the diameter of the particle 17 are formed in a bottom surface of the lower end 18, formed at the lower part of the thick tube 13. This prevents the particles 17 from entering the thick tube 13, and the particles 17 are entrapped in the capillary 15. Furthermore, eight projecting portions 16a projecting inward along the flowing direction of a fluid are provided on an inner wall of the leading end portion 19 to form a gap so as to prevent the particles 17 from tightly contacting the inner wall to impede the flow. The openings 18a, the projecting portion 16a, and the leading end portion 19 correspond to the entrapping portion. Reference numeral 14a denotes a projection provide on an outer surface of the installing opening 14. The size of the various-substance holder 11 according to the first embodiment is such that for example, the length of the thick tube is 1 to 10 cm and the length of the capillary portion is 1 to 10 cm. Furthermore, the diameter of the particles 17 is, for example, 0.1 to 3 mm. The inner diameter or the length of a cross section of the capillary 15 which is perpendicular to the axial direction of the capillary 15 are such that the particles can be held in a line.

Figure 3:
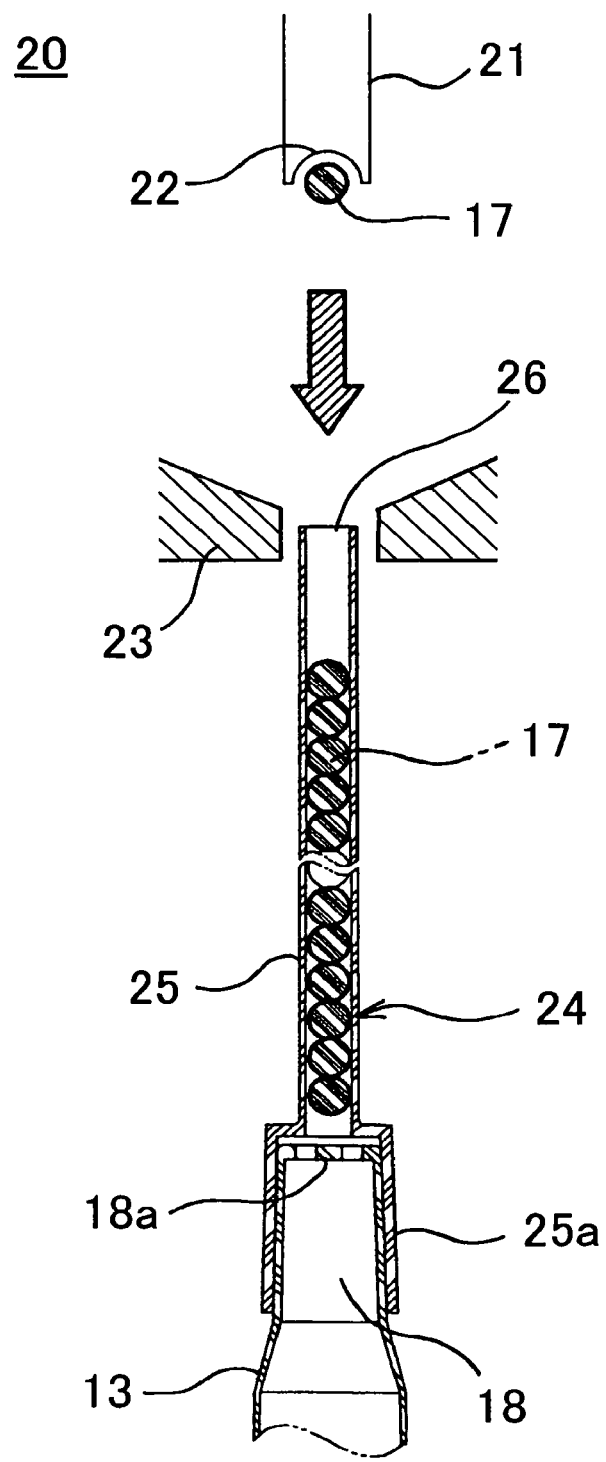
FIG. 3 is a schematic diagram showing a device manufacturing a various-substance holder according to a second embodiment.

FIG. 3 shows a carrier capturing and transferring portion 20 that captures and transfers the particles 17 as particulate carriers.

The figure shows that the carrier capturing and transferring portion 20 captures the particles 17 from the carrier holding portion (not shown), transfers the particles 17 to a tip-like container 24, and introduces and holds the particles 17 in the tip-like container 24.

Here, the carrier capturing and transferring portion has a sucking portion (not shown) that can suck gas, a tubular member 21 that is in communication with the sucking portion and which can capture the particles 17 as a result of the suction performed by the sucking portion, and tubular member moving means (not shown) capable of moving the tubular member relative to the tip-like container as the carrier holding portion.

Moreover, in the tip-like container 24 according to the second embodiment, unlike the tip-like container 12 according to the first embodiment, a leading end 26 of the capillary 25 has a tapered entrapping portion (not shown) removably attached thereto. An end of the capillary 25 which is opposite the leading end 26 has a fitting portion 25a into which the lower end 18 of the thick tube 13 is fitted. When the particles 17 are introduced into the capillary 25, the entrapping portion has been removed.

Furthermore, as shown in FIG. 3, the tip-like container 24 is installed with the leading end 26 directed upward. The tip-like container 24 is supported by a tip-like container support portion (not shown). The tip-like container 12 according to the first embodiment is installed with the installing opening 14 directed upward.

Furthermore, as shown in FIG. 3, an upward-broadening funnel-like guide 23 is provided so as to surround the periphery of the leading end 26. Additionally, a lower sucking mechanism (not shown) sucking gas through the installing opening, formed at the lower part of the thick tube 13, may be provided to reliably introduce the particles 17 into the capillary 25.

Figure 4:
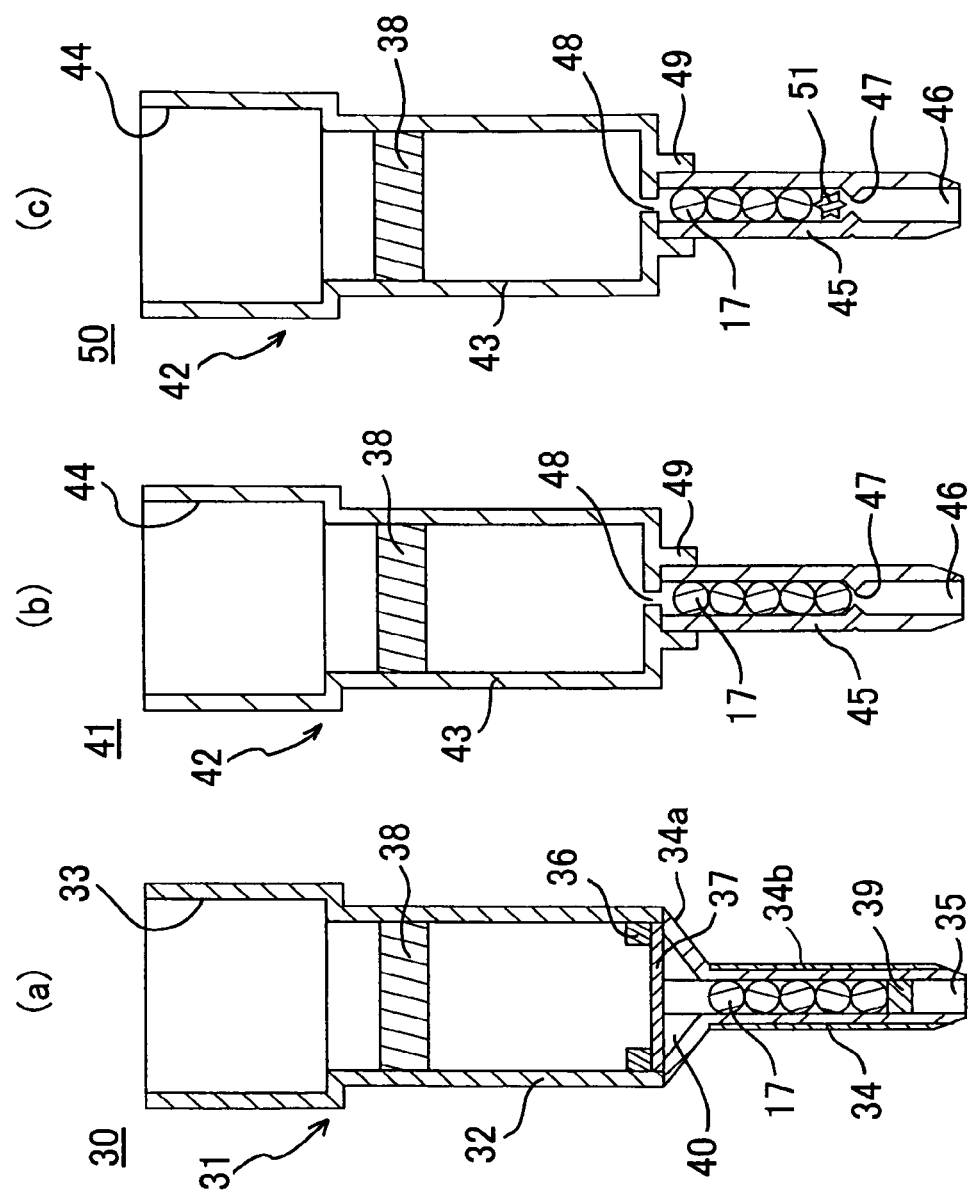
FIG. 4(a) is a sectional view of a various-substance holder according to a third embodiment.
FIG. 4(b) is a sectional view of a various-substance holder according to a fourth embodiment.
FIG. 4(c) is a sectional view of a various-substance holder according to a fifth embodiment.

FIGS. 4(a), 4(b), and 4(c) show various-substance holders 30, 41, and 50 according to a third embodiment to a fifth embodiment.

FIG. 4(a) shows a schematic sectional view of the various-substance holder 30 according to a third embodiment of the present invention. The various-substance holder 30 has a tip-like container 31 as the carrier holding portion and the particles 17 held in the tip-like container 31 and to which a plurality of (in this example, five; the number of the particles 17 is smaller than that in an actual case so that the figures are easier to see) the substances are or can be immobilized.

The tip-like container 31 has a thick tube 32 as the storage portion and a capillary 34 formed to be thinner than the thick tube 32. The tip-like container 31 is translucent. The thick tube 32 has an installing opening 33 formed at an upper end of the thick tube 32 and which is to be installed on a nozzle (not shown) used to suck and discharge gas. The capillary 34 has a mouth portion 35 formed at a leading end thereof and through which a fluid is allowed to flow in and out by sucking and discharging the gas. Each of the capillary 34 and the thick tube 32 has an outer surface and an inner surface each of which is formed substantially like a cylinder.

A filter 38 is fitted in the thick tube 32 slightly below the installing opening 33 so that the gas can pass through the filter 38. Furthermore, a substantially funnel-like transition portion 34a between the capillary 34 and the thick tube 32 is utilized to form a thin mesh-like member 37 as the carrier passage inhibiting portion. The transition portion 34a is held by a ring 36 located thereon. The transition portion 34a has a plurality of support plates 40 supported by the transition portion 34a, to support the mesh-like member 37. The plurality of (in this example, five) particles 17 as particulate carriers are accommodated in the capillary 34. A through porous member 39 as the carrier passage inhibiting member through which a fluid can pass is fitted in the capillary 34 below the particles 17. The through porous member 39 is preferably fitted in the capillary 34 utilizing a throttle or a step formed in the capillary 34. Here, the mesh-like member 37 and the through porous member 39 correspond to the entrapping portion.

Here, the outer diameter of each of the particles 17 as particulate carriers is, for example, about 1.8 mm. The inner diameter of the capillary 34 is about 2.0 mm. The length between the through porous member 39 and the mesh-like member 37 is, for example, about 50 mm.

Furthermore, if a large number of particles as particulate carriers are held, a particle that is colored or covered with a fluorescent substance as a reference particulate carrier is preferably held at a predetermined position.

The periphery of an outer side surface of the capillary 34 is coated with a translucent, conductive thin film 34b having a predetermined electric resistance. Passing current through the conductive thin film 34b enables an increase in the temperature of the capillary 34.

FIG. 4(b) shows a sectional view of the various-substance holder 41 according to the fourth embodiment of the present invention. The various-substance holder 41 has a tip-like container 42 as the carrier holding portion and the particles 17 held in the tip-like container 42 and to which a plurality of (in this example, five; the number of the particles 17 is smaller than that in an actual case so that the figures are easier to see) the substances are or can be immobilized.

The tip-like container 42 has a thick tube 43 as the storage portion and a capillary 45 formed to be thinner than the thick tube 43 and removably provided on the thick tube 43. The tip-like container 42 is translucent. The thick tube 43 has an installing opening 44 formed at an upper end of the thick tube 43 and which is to be installed on a nozzle (not shown) used to suck and discharge gas. The capillary 45 has a mouth portion 46 formed at a leading end thereof and through which a fluid is allowed to flow in and out by sucking and discharging the gas. The capillary 45 is fittably provided at an upper end of a fitting portion 49 provided so as to surround a hole 48 formed at a lower end of the thick tube 43 so as to extend through a central axis of the thick tube 43. When an upper end of the capillary 45 is fitted into the fitting portion 49, the capillary 45 is preferably ultrasonically or thermally welded to the fitting portion 49 or bonded to the fitting portion 49 with an adhesive, so as not to slip out from the fitting portion 49.

The tip-like container 42 is formed of, for example, glass, polyethylene, polystyrene, or polypropylene. Each of the capillary 45 and the thick tube 43 has an outer surface and an inner surface each of which is formed substantially like a cylinder.

The plurality of (in this example, five) particles 17 as particulate carriers are accommodated in the capillary 45. A projecting portion 47 is provided in a lower part of the capillary 45 and has a hole or cavity small enough to inhibit the particles 17 from passing through and projects in a radial direction of the capillary 45; the hole is formed so as to prevent the presence of the particles 17 from inhibiting the passage of the fluid. The size of the projecting portion 47, provided at the lower end of the capillary 45 is such that the particles 17 are prevented from passing through. The particles 17 are formed of, for example, a water-absorbing material, porous plastic, resin, or the like. The hole 48 and the projecting portion 47 correspond to the entrapping portion.

Here, for example, the capillary has an outer diameter of about 2.5 mm and an inner diameter of about 2 mm. Furthermore, the fitting portion 49 has an outer diameter of about 5 mm and an inner diameter equals to the outer diameter of the capillary. Furthermore, the length between the projecting portion 47 and the hole 48 is, for example, about 50 mm. The diameter of the hole 48 is set to, for example, about 1 mm so as to prevent the particles 17 from passing through. The length of the thick tube 43 is, for example, about 50 mm.

FIG. 4(c) shows a sectional view of a various-substance holder 50 according to a fifth embodiment of the present invention. The various-substance holder 50 employs a particle 51 having recesses and protrusions on a surface thereof instead of the lowermost one of the particles 17 entrapped in the capillary 45 unlike in the various-substance holder 41 according to the fourth embodiment, shown in FIG. 4(b).

Figure 5:
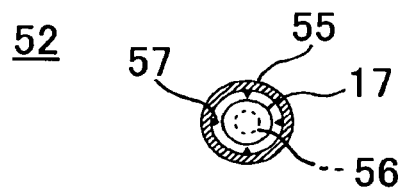
FIG. 5(a) is a plan view of a various-substance holder according to a sixth embodiment.
FIG. 5(b) is a sectional view of a various-substance holder according to the sixth embodiment.
Figure 5:
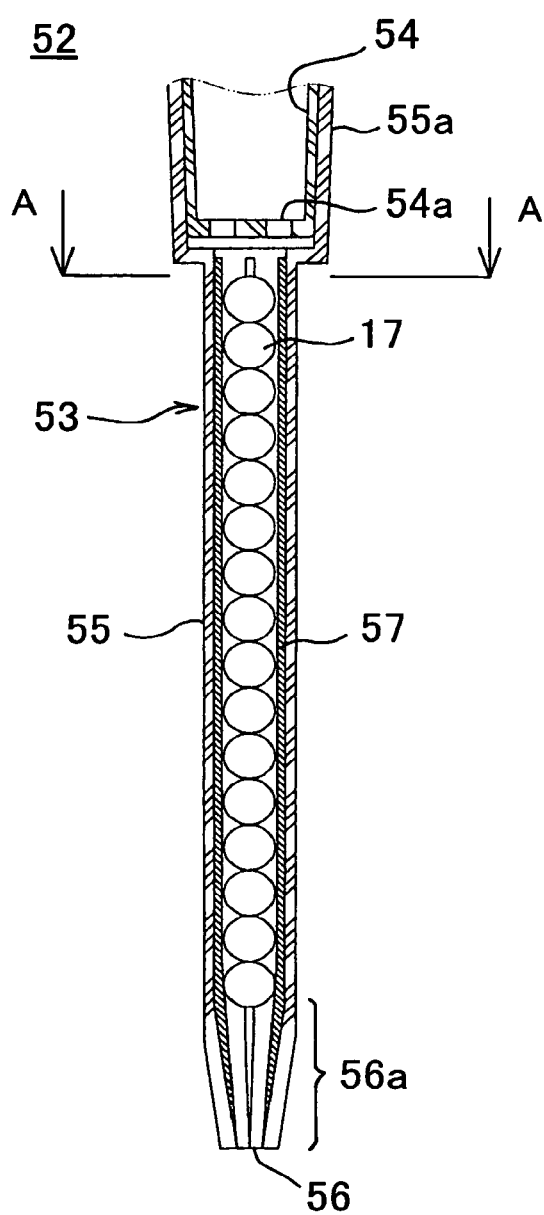

FIG. 5 is a schematic sectional view of a various-substance holder 52 according to a sixth embodiment. FIG. 5(a) is a sectional view of the various-substance holder 52 taken along line AA in FIG. 5(a). The various-substance holder 52 has a tip-like container 53 as the carrier holding portion and the particles 17 held in the tip-like container 53 and to which a plurality of (in this example, 15) the substances are or can be immobilized, the particles 17 being labeled with a labeling element such as a fluorescent substance so as to mutually identifiable. The tip-like container 53 has a fitting portion 55a installed at a lower end of the thick tube 54 as the storage portion and a capillary 55 formed to be thinner than a cylindrical portion of the thick tube 54. The tip-like container 53 is translucent. The thick tube 54 has an installing opening formed at an upper end thereof and which is to be installed around a nozzle (not shown) used to suck and discharge gas. A leading end portion 56a of the capillary 55 is tapered and has a mouth portion 56 at a leading end thereof. This makes it possible to suck and discharge the gas to allow a fluid to flow in and out through the mouth portion 56, while inhibiting the discharge of the particles 17. Radial openings 54a are formed at the bottom of the thick tube 54 and each have a length or width smaller than that of the particle 17. The openings 54a and the leading end portion 56a correspond to the entrapping portion. For example, the radial openings 54a are composed of a disc provided in the center thereof and bars supporting the disc and extending radially toward an inner peripheral surface of the thick tube 54.

Furthermore, the capillary 55 has four projections provided on an inner wall thereof along an axial direction joining the mouth portion 56 and the installing opening together; the projections 57 project in a direction in which the mouth portion 56 is partitioned from the installing opening. The projections 57 allow the fluid flowing in and out through the mouth portion 56 to flow smoothly in the cylindrical capillary 55 and to reliably contact with the particles 17.

Figure 6:
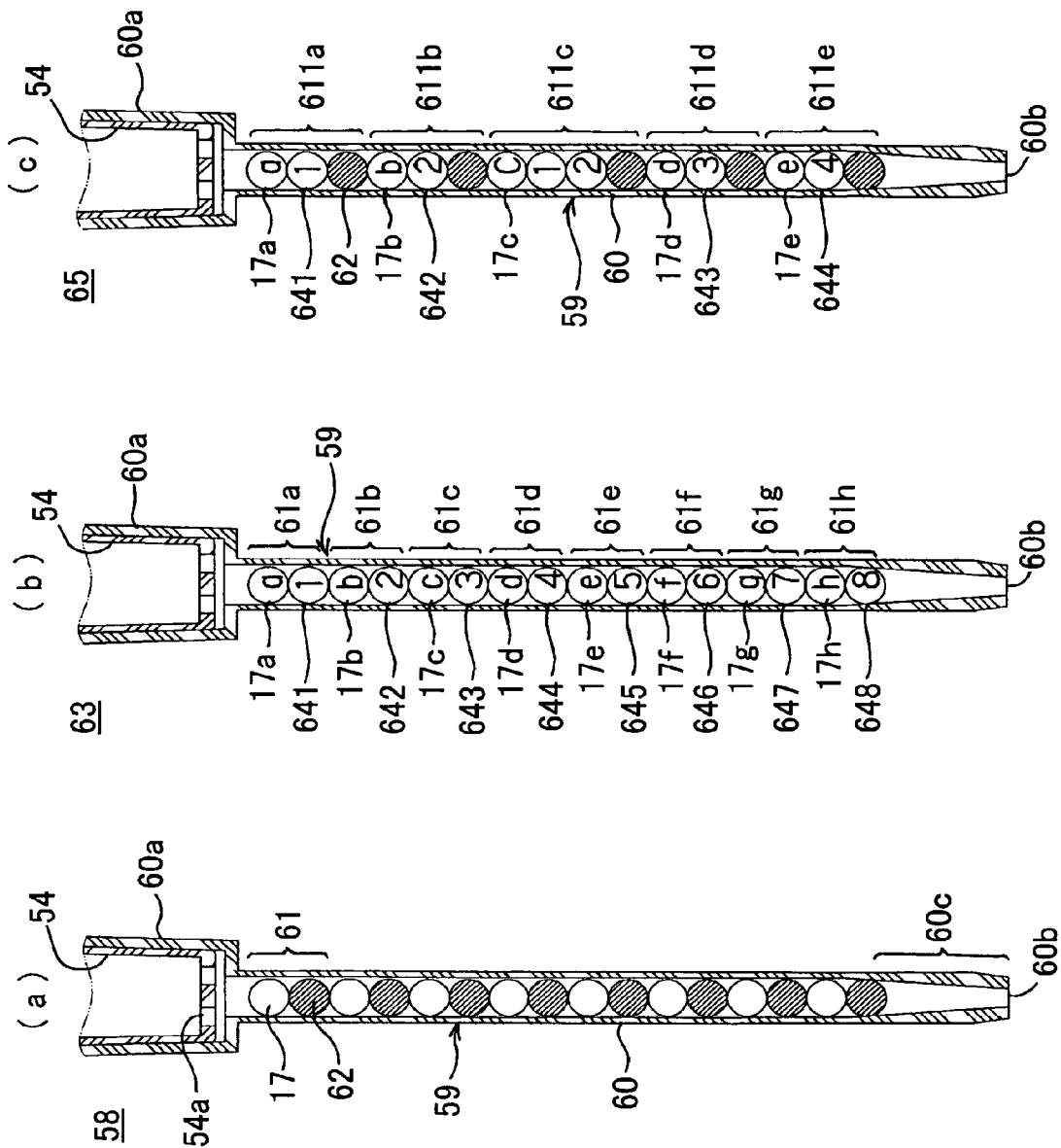
FIG. 6(a) is a sectional view of a various-substance holder according to a seventh embodiment.
FIG. 6(b) is a sectional view of a various-substance holder according to an eighth embodiment.
FIG. 6(c) is a sectional view of a various-substance holder according to a ninth embodiment.

FIG. 6 is a sectional view of various-substance holders 58, 63, and 65 according to a seventh embodiment to a ninth embodiment.

A various-substance holder 58 according to a seventh embodiment shown in FIG. 6(a) has a tip-like container 59 as the carrier holding portion, and a plurality of (in this example, eight) particle aggregates 61 as plural sets of particulate carriers held in the tip-like container 59 and including the particles 17 to which the various substances are or can be immobilized and which are labeled with, for example, a fluorescent substance so as to be mutually identifiable and a blocking particle 62 as a boundary particle that blocks light from the fluorescent substance so as to prevent the light from reaching the adjacent particle aggregate 61. The blocking particle 62 has only to be opaque and may be, for example, a metal particle or a resin particle formed of plastics or the like. The tip-like container 59 has a fitting portion 60a installed around a lower end of the thick tube 54 as the base storage portion and a capillary 60 formed to be thinner than a cylindrical portion of the thick tube 54. The tip-like container 59 is translucent. The thick tube 54 has an installing opening formed at an upper end thereof and which is to be installed on a nozzle (not shown) used to suck and discharge gas.

An inner surface of the capillary 60 is formed like, for example, a prism such that a liquid is allowed to flow smoothly along the capillary 60 by sucking and discharging gas through the nozzle even when the particles 17 or the like are held inside the capillary 60. A leading end portion 60c of the capillary 60 is tapered and has a mouth portion 60b formed at a leading end thereof so that a fluid is allowed to flow in and out through the mouth portion 56 by sucking and discharging the gas, with the discharge of the particles 17 inhibited. The radial openings 54a are formed at the bottom of the thick tube 54 and each have an inner diameter smaller than the diameter of the particle 17. The leading end portion 60c and the openings 54a correspond to the entrapping portion.

A various-substance holder 63 according to an eighth embodiment shown in FIG. 6(b) has the tip-like container 59 as the carrier holding portion, and particle aggregates 61a to 61h as plural sets (in this example, eight) of particulate carriers held in the tip-like container 59. The particle aggregates 61a to 61h have reacting particles 17a to 17h as particulate carriers, respectively, to which different biological substances as various substances are or can be immobilized and labeling particles 641 to 648 as particulate carriers, respectively, to which a labeling substance enabling the various substances to be mutually identified is immobilized.

A various-substance holder 65 according to a ninth embodiment shown in FIG. 6(c) has the tip-like container 59 as the carrier holding portion, and particle aggregates 611a to 611e as plural sets (in this example, five) of particulate carriers held in the tip-like container 59. The particle aggregates 611a to 611e have the reacting particles 17a to 17e as particulate carriers, respectively, to which different biological substances as various substances are or can be immobilized and the labeling particles 641 to 644 as particulate carriers, respectively, to which a labeling substance enabling the various substances to be mutually identified is immobilized. However, unlike the various-substance holder 63 according to the eighth embodiment, the number of particulate carriers belonging to the particle aggregate varies among the particle aggregates 611a to 611e. Furthermore, the number (four) of labeling particles 641 to 644 is smaller than the number (five) of the particle aggregates 611a to 611e for mutual identification.

The present embodiment also differs from the eighth embodiment in that the blocking particle 62 is provided in each of the aggregates as a boundary particle.

Figure 7:
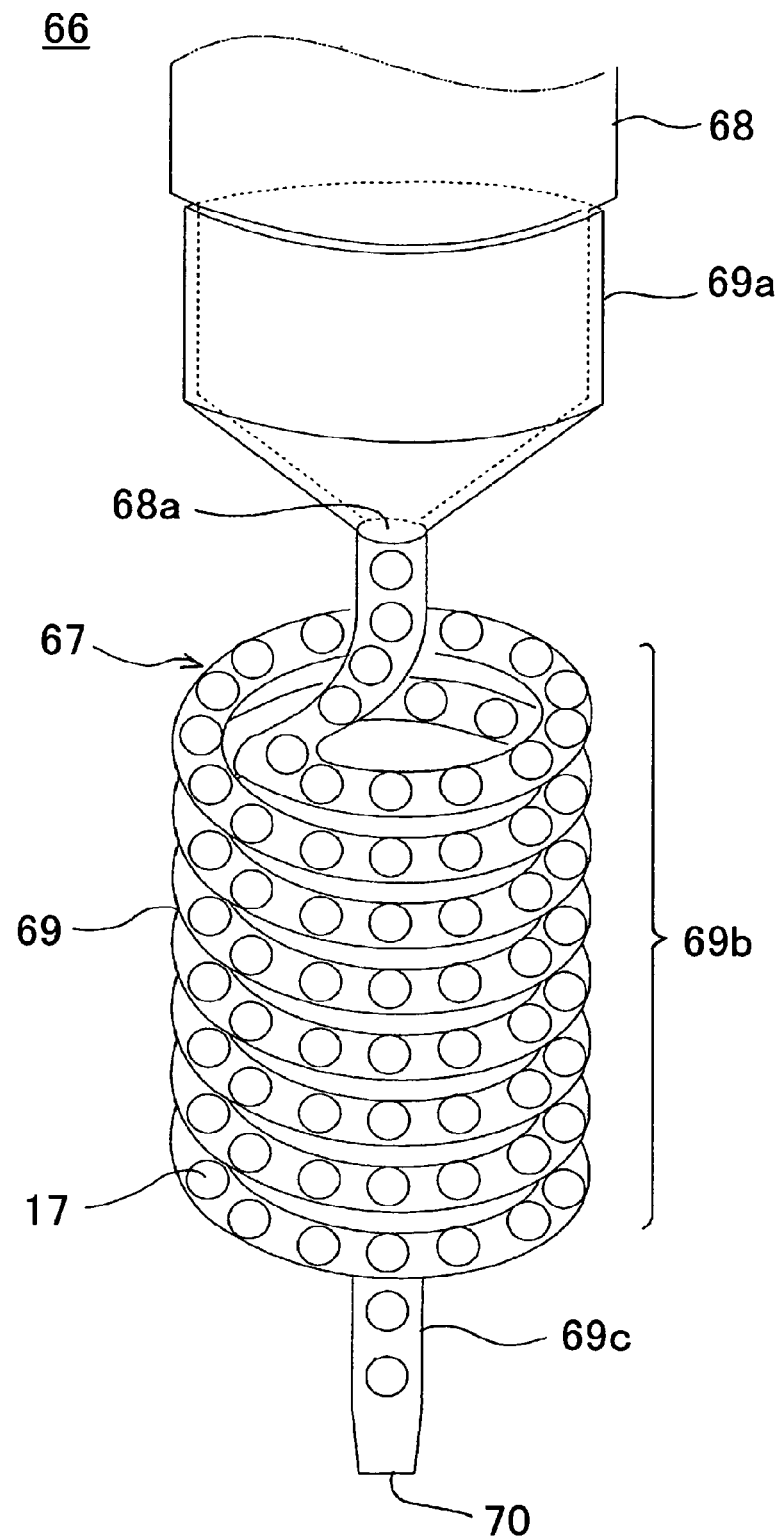
FIG. 7 is a schematic view of a various-substance holder according to a tenth embodiment.

FIG. 7 shows a perspective view of the various-substance holder 66 according to a tenth embodiment. The various-substance holder 66 has a tip-like container 67 as the carrier holding portion and the particles 17 held in the tip-like container 67 and to which a plurality of the substances are or can be immobilized, the particles 17 being labeled so as to be mutually identifiable. The tip-like container 67 has a fitting portion 69a installed at a lower end of a thick tube 68 as the storage portion and a capillary 69 formed to be thinner than a cylindrical portion of the thick tube 68. The tip-like container 67 is translucent. The thick tube 68 has an installing opening formed at an upper end thereof and which is to be installed on a nozzle (not shown) used to suck and discharge gas.

As shown in FIG. 7, the capillary 69 has a fitting portion 69a installed at the lower end of the thick tube 68, a spiral portion 69b spirally formed so as to turn around an axis joining the installing opening in the thick tube 68 and a mouth portion 70, and a linear portion 69c linearly formed along the axial direction so as to be insertable into various containers and has a tapered leading end portion with the mouth portion 70. The particles 17 are held in the capillary 69. In the various-substance holder 66 according to the tenth embodiment, the capillary 69 has the spiral portion 69b, formed to turn spirally around the axis, a large number of particulate carriers can be compactly held, eliminating the need for a large space and improving the rigidity of the holder. Furthermore, measurements can be easily performed by receiving light from the particles 17 so that the particles 17 are scanned along the capillary 69.

Figure 8:
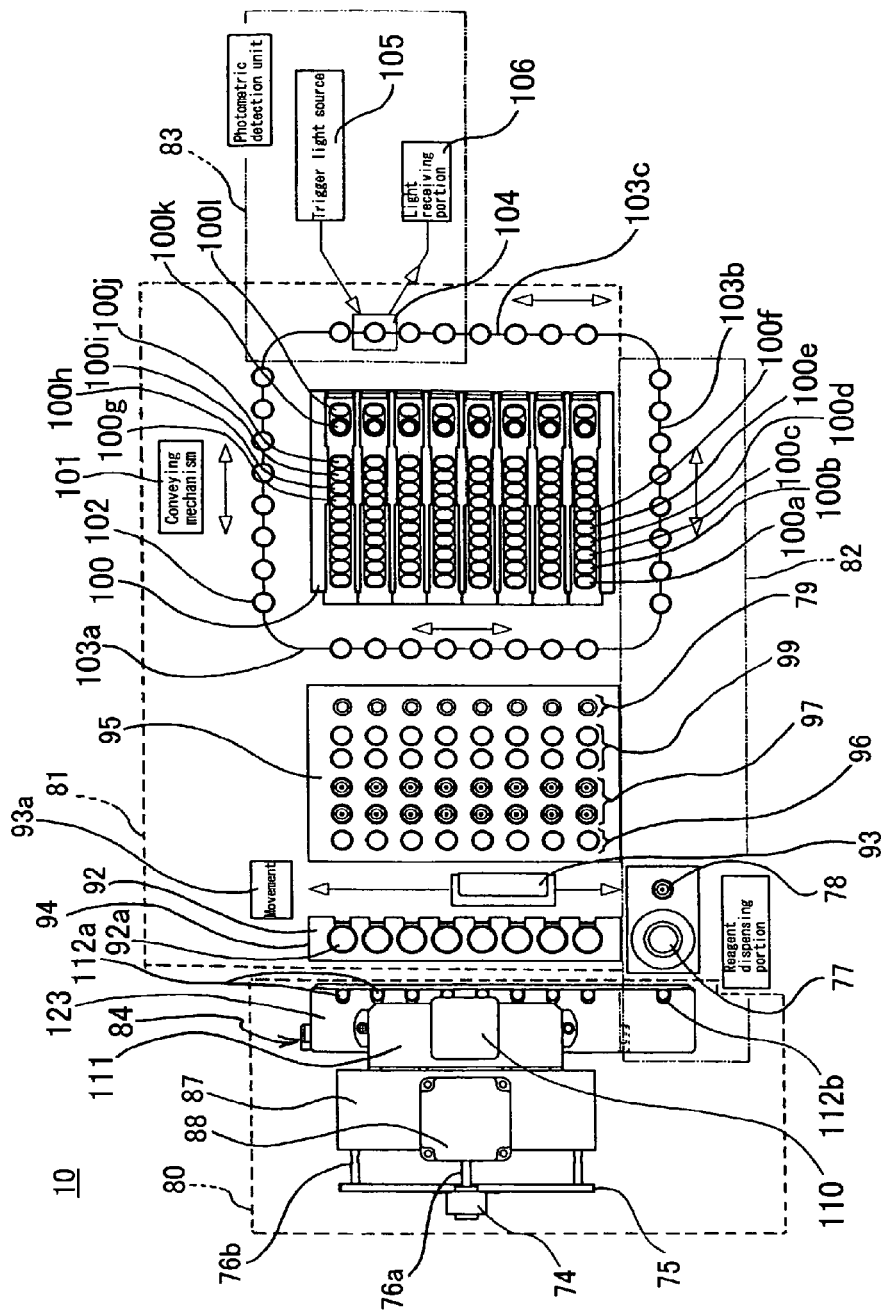
FIG. 8 is a schematic plan view showing an entire various-substance holder treating apparatus according to an eleventh embodiment.

FIG. 8 is a schematic plan view showing an entire various-substance treating apparatus 10 according to an eleventh embodiment of the present invention.

The various-substance treating apparatus 10 includes a various-substance holder treating apparatus 80 having a suction and discharge mechanism to perform a sucking and discharging treatment on the various-substance holder 11 installed on the nozzle, a various-substance holder treatment area 81 in which a suspension containing various samples, reagents, and the like is sucked into or discharged from the various-substance holder 11 to suck and discharge the suspension for the particles 17, dispense the suspension to an external container, or achieve agitation, cleaning, extraction, transfer, or reaction, a reagent dispensation area 82 in which one of the nozzles in the various-substance holder treating apparatus 80 is used to dispense reagents for measurements or the like into the tip-like container 12 in the various-substance holder 11, and a measurement area 83 in which optical information is obtained in order to measure the particles 17 entrapped in the various-substance holder 11.

Figure 9:
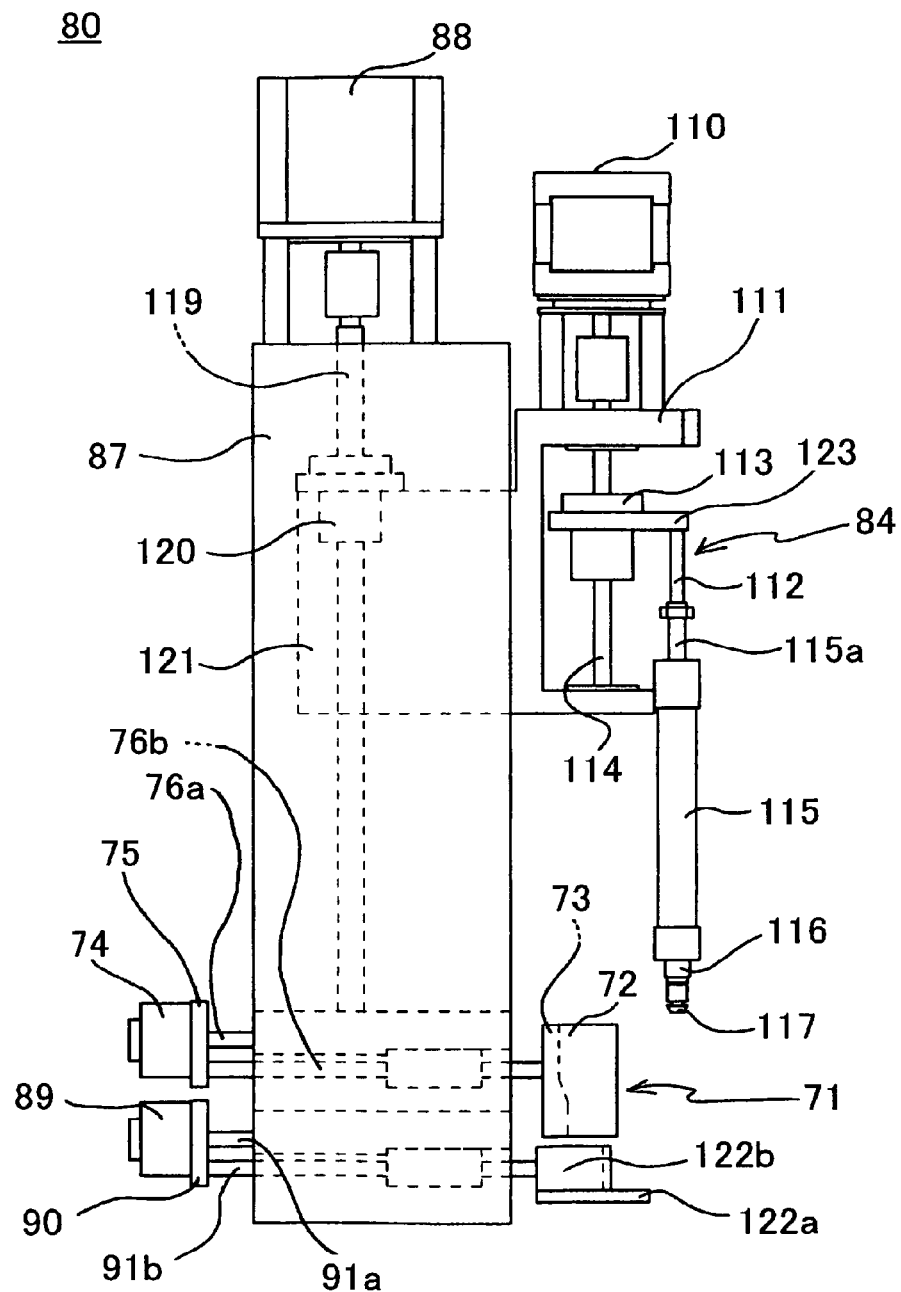
FIG. 9 is a side view showing the various-substance holder treating apparatus according to the eleventh embodiment.

The various-substance holder treating apparatus 80, shown in FIGS. 8 and 9, uses the nozzle that is in communication with the suction and discharge mechanism to suck and discharge the gas. The various-substance holder treating apparatus 80 has nozzle heads 84 each having a series of a plurality of (in this example, nine) nozzles arranged in a column direction (a vertical direction in the drawings). A sucking and discharging operation is performed on all the nozzle heads 84 at a time. One of the nine nozzles 117 located at an end of the series of nozzles is a separate nozzle and lies somewhat away from the positions (shown by reference numeral 112a in FIG.

8) of the eight nozzles 117, that is, the batch nozzles, as shown by the position (shown by reference numeral 112b in FIG. 8) of the separate nozzle.

As shown in FIG. 9, the suction and discharge mechanism has a larger diameter portion 116 provided somewhat above each of the nozzles 117, and a rod 112 that slides a plunger 115a through a cylinder 115 combined with the nozzle 117. Moreover, the nine rods 112 are mounted so that eight ends 112a and one end 112b each having a larger diameter than the rod 112 and projecting in a radial direction are hooked in nine notches formed at edges of driving plates 123 that can be moved up and down in union. The nozzle heads 84 are moved in union in a row direction (a horizontal or lateral direction on the drawings).

Furthermore, as shown in FIG. 9, each of the driving plates 123 is coupled to a nut portion 113 threadably fitted around with a ball screw 114. Each of the rods 112 is always biased downward by a spring provided in the cylinder 115. Thus, to be moved upward, the rod 112 is elevated by the nut portion 113, whereas to be moved downward, the rod 112 is lowered by the force of the spring instead of the nut portion 113. The ball screw 114 is rotationally driven by a motor 110 provided on a support member 111 with a U-shaped cross section. This moves the driving plates 123 and the nine rods 112 upward or downward in union.

Since the separate nozzle, one of the nine nozzles 117, is provided in the nozzle head 84, the separate nozzle is subjected to suction and discharge in union with the other, eight batch nozzles. The elevating and lowering mechanism also performs these concurrent operations, and the horizontal movement in the row direction (the lateral direction in FIG. 8) is also concurrently performed. However, the separate nozzle is used to dispense a measuring regent into the various-substance holder 11 in the reagent dispensation area 82. The separate nozzle is used with the various-substance holders removed from the other, batch nozzles. Furthermore, the batch nozzles are used with the tip-like container or the like not installed in the separate nozzle.

In FIG. 9, a housing 87 contains a ball screw 119, a nut portion 120 threadably fitted around the ball screw 119, and a support 121 having, at one end, the support member 111 attached to the nut portion 120. Furthermore, a motor 88 rotationally driving the ball screw 119 is provided on the housing 87. A vertical movement mechanism composed of these parts can move the nozzles 117 in the vertical direction.

Temperature increasing and reducing means 71 is provided at a lower part of the housing 87. The temperature increasing and reducing means 71 is formed along the column direction so as to have a height and width such that the temperature increasing and reducing means 71 can approach and contact the nine various-substance holders 11 installed on the respective nozzles and mainly the capillaries 15 thereof. The temperature increasing and reducing means 71 contains a heating wall 72 containing a heater and 10 heating plates 73 mounted on the heating wall 72 and projecting so as to sandwich each tip between the adjacent heating plates, the heating plates each containing a heater. The heating wall 72 is preferably shaped in conformity to the shape of the tips to be subjected to temperature control. Here, the heating wall 72 and the heating plates 73 correspond to the temperature increasing and reducing member.

The temperature increasing and reducing means 71 has a motor 74 that makes it possible to approach and contact the various-substance holder 11 installed on the nozzle in the nozzle head 84 to heat the tip, a ball screw 76a rotationally driven by the motor 74, a nut portion 75 threadably fitted around the ball screw 76a, and a moving rod 76b which is coupled to the nut portion 75 so as to be movable in the lateral direction on the figure and which is also coupled to the heating wall 72 and the heating plates 73.

The following are provided below the temperature increasing and reducing means 71: a comb teeth-like pawl 122a and nine magnets 122b, a motor 89 that makes it possible to move the various-substance holder 11 installed on the nozzle 117 in the lateral direction on the figure for removal or to apply a magnetic field to the various-substance holder 11, a moving support plate 90 that is movable in the lateral direction by means of the motor 89, and moving rods 91a and 91b attached to the moving support plate 90.

The various-substance holder treating apparatus 80 is provided so as to hang from above and to be movable by means of an X-axis (row-direction) moving mechanism that utilizes a direct-acting mechanism (not shown) so that the various-substance holder treating apparatus 80 covers the entire various-substance treating apparatus 10 and other required areas.

Referring back to FIG. 8, the various-substance holder treatment area 81 includes a cartridge container 92 having eight well columns 92a that accommodate suspensions in which samples are suspended, a matrix-like container 95 made up of 6.times.8 wells and having a well column 79 that accommodates the capillaries of the various-substance holders, well columns 96 and 99 that accommodate target substances extracted from various products or subjects or particulate carriers, for example, reacting particles, labeling particles, or blocking particles, and a well column 97 that accommodates the capillary portions of the various-substance holders 11, having the capillaries, or the thick tube portions thereof, having the thick tubes installed on the capillary portions, and eight cartridge containers 100 each having pre-packable wells 100a to 100l that accommodate various reagents required to perform the treatments, various fluorescent substances, or treatment results. Reference numerals 100k and 100l on the cartridge containers 100 denote a spare incubator well and an incubator well each having a heart block. Furthermore, the tubular member 21 may be removably installed on the nozzle 117 so that the nozzle can capture and transfer the particles 17.

Moreover, the well column 92a, which accommodates the target substances such as samples, has bar codes 92b providing information on the target substances. The bar codes 92b are read by a bar code reading section 93 that moves so as to scan and read the bar codes 92b. Reference numeral 93a denotes a moving mechanism that drives the bar code reading section 93.

A conveyor 103 is provided so as to surround the periphery of the eight cartridge containers 100 and is movable along a quadrangular conveyance path having column conveyance paths 103a and 103c extending along a column direction (the vertical direction on the drawing; a Y direction) parallel to the direction in which the eight nozzles are arranged, on a moving path of the eight nozzles 117 (batch nozzles) of the various-substance holder treating apparatus 80, and a row conveyance path 103b extending along a row direction (the horizontal direction; an X direction) on a moving path of the single nozzle 117 (separate nozzle).

The conveyor 103 corresponds to the row and column path conveying means and has a total of 32 tip accommodating portions (or tubes) 102 coupled thereto in association with the intervals among the nozzles so as to be movable together with the conveyor 103. Consequently, in such a position as shown in FIG. 8, the eight nozzles 117 in the various-substance holder treating apparatus 80 can suck and discharge a liquid into and from the two columns of tip accommodating portions 102, arranged on the column conveyance paths 103a and 103c. Furthermore, the nozzle 117 (separate nozzle), provided away from the group of the eight batch nozzles in the various-substance holder treating apparatus 80, can dispense an appropriate reagent, for example, a substrate solution for chemiluminescence, to the selected tip accommodating portions (or tubes) 102 on one of the conveyance paths arranged like a quadrangle as the row and column path conveying means, the row conveyance path 103b on the bottom side, that is, the selected tip accommodating portions (or tubes) 102 in the reagent dispensation area 82. In particular, in a PCR pretreatment for DNA extraction, a PCR reaction solution or the like is dispensed immediately before reaction.

Moreover, a measurement point 104 is provided in the measurement area 83 in the quadrangular conveyance path of the row and column path conveying means. At the measurement point 104, a trigger light source 105 irradiates the interior of the various-substance holder with excitation light. A light receiving portion 106 then receives the resulting light for measurement. This allows appropriate treatments to be performed on each various-substance holder 11.

Although not shown, to control the various-substance treating apparatus 10, an information processing apparatus gives instructions to and receives signals from the suction and discharge mechanism, moving mechanism, row and column path conveying means, devices in the measurement area 83, and the like in the various-substance holder treating apparatus 80; the information processing apparatus has an input device via which a user inputs instructions and data, a CPU that executes processes such as various arithmetic operations, a display device, various memories, transmission means, and the like. The information processing apparatus has a control section that controls the amount, speed, count, time, or position of the suction or discharge through the nozzle on the basis of the substance conditions including the structure of the nozzle, the members installed in the nozzle, or the various-substance holder, the type and concentration of the substance present in the fluid, the amount of the fluid, the temperature of the fluid or carrier, and the coordinate positions including the position where the fluid is accommodated, as well as the contents of the treatment.

Figure 10:
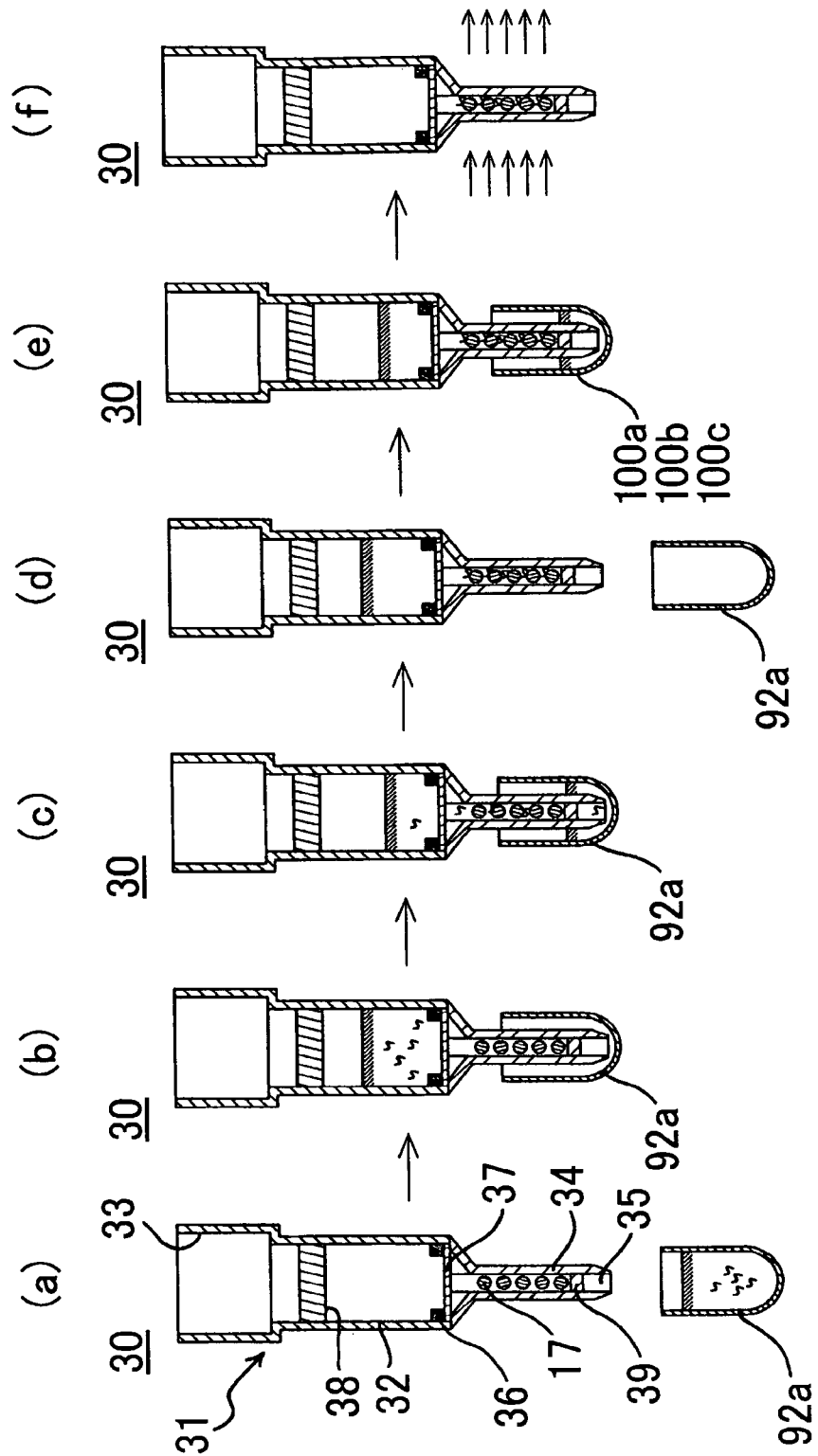
FIG. 10 is a flowchart showing a method for treating a various-substance holder according to a twelfth embodiment.

Now, with reference to FIG. 10, description will be given of an example in which the various-substance holder 30 is used for DNA SNPs (single nucleotide polymorphisms) typing, as a various-substance holder treating method according to a twelfth embodiment.

Four types of oligonucleotides having base sequences that are likely to be hybridized at a plurality of SNP positions to be measured are immobilized, as a probe substance, to four of the plurality of (in this example, five) particles 17, respectively. For immobilization to the particles 17, a functional group is pre-generated or -expressed on the surface of each of the particles 17 and bonded to the probe substance. The surface of the particle 17 is then cleaned using an appropriate solvent.

For example, it is assumed that at SNP1 (a first position), two types, a basic T and a basic C, are possible and that at SNP2 (a second position), two types, a basic G and a basic A, are possible. That is, the four types of basics T, C, G, and A are possible.

The following are immobilized to the particles 17: a base sequence for T determination at SNP1, a base sequence for C determination at SNP1, a base sequence for G determination at SNP2, and a base sequence for A determination at SNP2. The particles 17 to which the four different types of basic sequences are immobilized are labeled with predetermined four types of fluorescent substances, that is, four different types of fluorescent substances selected from, for example, organic substances such as FITC (Fluorescein isotiocyanate), rhodamine, isothiacyanate, IRD40, CY3, and CY5 and inorganic substances such as an europium complex which emit long-lasting fluorescence, so that the particles 17 are mutually identifiable. Here, light from the fluorescent substances used to mutually identify the particles 17 corresponds to signals based on the first label.

As shown in FIG. 10(a), the through porous member 39 is provided in the capillary 34 of each of the eight translucent tip-like containers 31. The five particles 17 including those to which the base sequence and the fluorescent substances are immobilized (one of the particles 17 has no base sequence or label) are placed in the capillary 34 in an arbitrary or optional order. The mesh-like member 37 is provided in the capillary 34 for entrapment. The eight various-substance holders 30 are thus formed.

Description will be given of the case where for example, a plurality of (in this case, two) SNPs typing positions are simultaneously determined for eight subjects. In this case, in step S1, the installing opening 33, formed at the upper end of the thick tube 32 of each of the eight various-substance holders 30 thus formed, is installed on one of the eight nozzles 117 in the various-substance holder treating apparatus 80.

Samples described below are accommodated in the well column 92a, provided in the various-substance holder treatment area 81 so as to accommodate eight samples. That is, genomes are extracted from blood from the eight subjects. A fraction of each of the genomes which contains a plurality of the SNPs typing positions is amplified by a thermal cycler and labeled with a fluorescent substance. The resulting genomes are accommodated in the well column 92a accommodating the eight samples for the respective subjects. A BW buffer solution is accommodated in the wells 100a to 100c in each of the eight cartridge containers 100.

In step S2, as shown in FIG. 10(b), the nozzle head 84 of the various-substance holder treating apparatus 80 is advanced in the row direction by the moving means to insert the eight capillaries 34 into the well column 92a in union. The suspension in the well column 92a is sucked and filled into the capillaries 34 at a time.

In step S3, as shown in FIG. 10(c), the sucking and discharging operation is repeated, for example, 10 times at a predetermined speed s1 (for example, about 200 litters/sec) by an amount v1 (for example, about 400 litters) for agitation. Thus, the plurality of particles 17 and the suspension in the capillary 34 are sufficiently contacted with each other. At this time, to facilitate reaction, temperature control is performed by passing a predetermined current through the conductive thin film 34b.

Then, in step S4, as shown in FIG. 10(d), each of the DNA fractions in the suspension which have been labeled with the fluorescent substances are bonded by hybridization to the particle 17 corresponding to the SNP position of that DNA fraction. The remaining solution is discharged into the well column 92a. Here, the fluorescent substance labeling the DNA fraction is of a type different from the four types of the fluorescent substances used to identify the base sequences immobilized to the particles 17. A signal from this fluorescent substance corresponds to the signal based on the second label.

In step S5, as shown in FIG. 10(e), the various-substance holder treating apparatus 80 transfers the various-substance holder 30 with the reacted particles 17 entrapped therein to the position of the well 100a in one of the eight cartridge container 100. The various-substance holder treating apparatus 80 cleans the BW buffer solution by repeating the operation of sucking and discharging the solution 10 times, for example, at a predetermined speed s2 (for example, about 760 to 1,700 μlitter/sec) by a very small amount v2, for example, several tens of litters to several hundred μlitters (for example, about 500 μlitters). The various-substance holder treating apparatus 80 repeats a similar operation on the wells 100b and 100c.

In step S6, as shown in FIG. 10(f), the nozzle head 84 is moved by the cleaned various-substance holders 30 to the position of the tip accommodating portions (or tubes) 102 stopped on the column conveyance path 103a of the conveyor 103. The cleaned various-substance holders 30 are then released, via the pawl 122a, from the plurality of batch nozzles (117), formed in the nozzle head 84, and accommodated in the tip accommodating portions 102. The conveyor 103 is then driven to convey the various-substance holders 30 along the conveyance path. Once the tip accommodating portions 102 reach the row conveyance path 103b, the whole nozzle head 84 is moved so that the separate nozzle (117) is located at the position where the dispensing tip 78 is accommodated. The nozzle head 84 is then lowered to install the dispensing tip 78 only on the separate nozzle. The nozzle head 84 is further moved to the reagent accommodating portion 77 to suck the predetermined reagent. The nozzle head 84 then dispenses the predetermined reagent, for example, a measuring reagent, through the installing opening 33 in a selected one of the various-substance holders 30 in the eight tip accommodating portions 102 stopped along the row conveyance path 103b. The conveyor 103 is subsequently driven to convey the tip accommodating portions 102 to the measurement point 104, provided on the conveyance path. At the measurement point 104, each of the tip accommodating portions 102 is irradiated with excitation light, and the light receiving portion 106 receives light from the interior of the capillary 34. In this case, the combination of the signal based on the first label and the signal based on the second label is measured to analyze the structure of the target substance.

Figure 11:
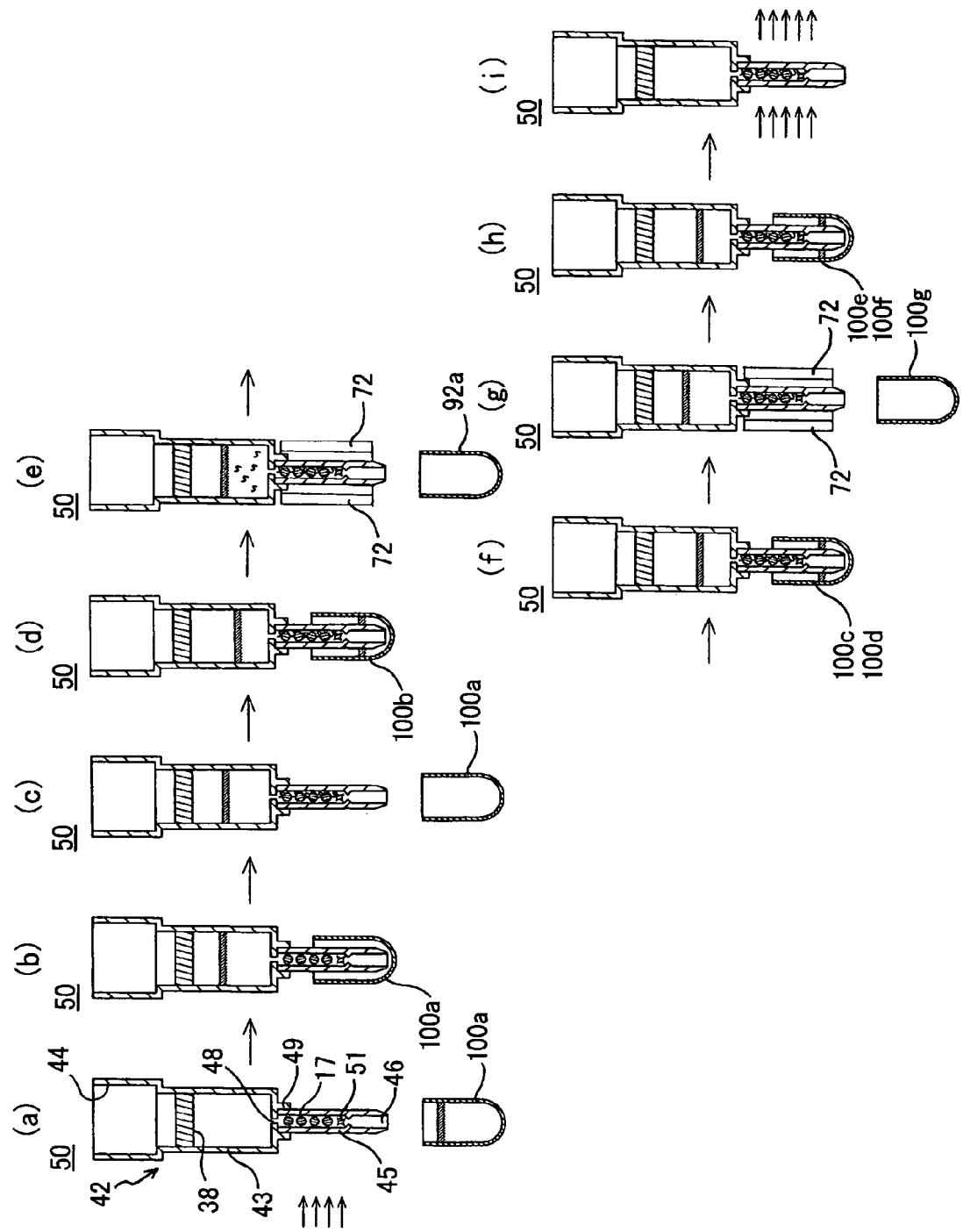
FIG. 11 is a flowchart showing a method for treating a various-substance holder according to a thirteenth embodiment.

Now, with reference to FIG. 11, description will be given of the case where a various-substance holder treating procedure according to a thirteenth embodiment for allergy tests is executed using the various-substance holder 50, as an example of analysis of protein.

Various allergen substances, for example, four types of substances obtained from cedar pollen, hogweed, mice, and mold are immobilized to the respective particles 17. To allow the allergen substances to be immobilized to the particles 17, a functional group is pre-generated or -expressed on the surface of each of the particles 17. The particles 17 to which the four types of allergen substances are immobilized are labeled with four mutually-identifiable different types of fluorescent substances selected from, for example, the above-described fluorescent substances, so that the particles 17 are mutually identifiable. Here, light from the fluorescent substances used to mutually identify the particles 17 corresponds to the signal based on the first label.

As shown in FIG. 11(a), in step S11, the capillaries 45 of the eight translucent tip-like containers 42, shown in FIG. 4(c), are accommodated in the eight wells in the well column 99. A particle 51 with recesses and protrusions is placed in each of the respective capillaries 45. Then, the four particles 17 including those to which the allergen substances and the fluorescent substances are immobilized are placed in the capillary 45 in an arbitrary or optional order. Finally, the installing opening 44, formed at the upper end of the thick tube 43 of the thick tube portion accommodated in the well column 97, is installed on the nozzle 117, and the capillary 45 is then moved. The capillary 45 is then fitted into the fitting portion 49 in such a manner that the fitting portion 49 is pressed against the capillary 45. The capillary 45 is then attached to the fitting portion 49 by bonding, ultrasonic or thermal welding, or the like to entrap the particles. The eight various-substance holders 50 are thus formed.

On the other hand, blood serums collected from eight subjects are accommodated in the well column 92a, formed in the various-substance holder treatment area 81 to accommodate the samples. 50 mM of TBS buffer solution and a 1% BSA solution of pH8 are accommodated in the well 100a in each of the eight cartridge containers 100. A cleaning fluid made up of 50 mM of TBS buffer solution and a 0.005% Tween solution of pH8 is accommodated in each of the wells 100b to 100f. A solution in which an antihuman IgE antibody labeled with a fluorescent substance is suspended is accommodated in the well 100g. The fluorescent substance labeling the antihuman IgE antibody is different from, of a type different from the four types of fluorescent substances identifying the allergen substances immobilized to the particles 17.

At this stage, the nozzle head 84 is moved to the position of the tip accommodating portions 102 stopped on the column conveyance path 103a of the conveyor 103. The various-substance holders 50 are then released, via the pawl 122a, from the eight batch nozzles (117), formed in the nozzle head 84. The various-substance holders 50 are then accommodated in the tip accommodating portions 102, arranged on the column conveyance path 103a. The conveyor 103 is then driven to convey the various-substance holders 30 along the conveyance path. Once the tip accommodating portions 102 reach the position of the row conveyance path 103b, the separate nozzle 117 is moved to the reagent accommodating portion 77, which accommodates the predetermined reagent. The separate nozzle 117 sucks the predetermined reagent if required, and then moves to a selected one of the various-substance holders 50 in the eight tip accommodating portions 102 stopped along the row conveyance path 103b. The separate nozzle 117 then dispenses the predetermined reagent through the installing opening 44 in the various-substance holder 50. Then, at the measurement point 104, provided on the conveyance path, the light receiving portion 106 receives light from the particles 17. This enables the particles 17 to be identified on the basis of signals based on the first label, allowing the label information to be read from each of the particles 17. The label information is stored in the memory as a control section.

In step S12, as shown in FIGS. 11(a), 11(b), and 11(c), the solution accommodated in the well 100a is agitated by sucking and discharging the solution at a speed s3 (for example, about 760 μlitters/sec) by an amount v3 (for example, about 500 μlitters). The surfaces of the particles 17 are thus blocked.

In step S13, as shown in FIG. 11(d), the particles are cleaned in the 50 mM of TBS buffer solution and 0.005% Tween solution of pH8 accommodated in the well 100b on the cartridge container 100. In step S14, as shown in FIG. 11(e), the various-substance holder 50 installed in the nozzle is moved to the well column 92a, which accommodates samples. The various-substance holder 50 then sucks the blood serum accommodated in the well column 92a into the capillary 45 for contact and maintains the interior of the capillary 45 at about 37.degree. C. for 30 minutes so that the IgE antibody reacts with the allergen substance. At this time, to be maintained at a constant temperature, the capillary 45 is heated by moving the heating wall 72, sandwiched between the heating plates 73 of the temperature increasing and reducing means 71, closer to the eight various-substance holders 50 so that the capillary 45 is sandwiched between the heating plates 73; the heating plates 73 are arranged like comb teeth. The interior of the capillary 45 can be efficiently and reliably heated.

Then, in step S15, as shown in FIG. 11(f), the various-substance holder 50 is moved to the well 100c on the cartridge container 100. The above-described cleaning fluid is accommodated in the well 100c. For example, the cleaning is performed by repeating the sucking and discharging operation 10 times at a speed s4 (for example, 760 μlitters to 1,700 μlitters) by an amount v4 (for example, about 500 μlitters). Moreover, the various-substance holder 41 is transferred to the well 10d, where the cleaning is repeated.

Then, in step S16, as shown in FIG. 11(g), the nozzle head 84 is moved to the well 100g and is allowed to suck the suspension so that the particles 17 contact and react with the antihuman IgE antibody accommodated in the well 100g and labeled with the fluorescent substance. The particles 17 are maintained at about 37.degree. C. for 30 minutes. Also in this case, as described above, the interior of the capillary 45 is heated by moving the heating wall 72 of the temperature increasing and reducing means 71 closer to the various-substance holder 50.

Then, in step S17, as shown in FIG. 11(h), the various-substance holder 50 is moved to the well 100e on the cartridge container 100. The particles 17 are then cleaned by performing the suction and discharge of the cleaning fluid accommodated in the well 100e, about 10 times at a speed s5 (for example, 760 μlitters to 1,700 μlitters) by an amount v5 (for example, about 500 μlitters). The various-substance holder 50 is then moved to the well 100f, where the same operation is repeated.

Then, in step S18, as shown in FIG. 11(i), the nozzle head 84 is moved to the tip accommodating portions 102 stopped on the column conveyance path 103a of the conveyor 103. The various-substance holders 50 are then released, via the pawl 122a, from the eight batch nozzles 117, formed in the nozzle head 84. The various-substance holders 50 are then accommodated in the tip accommodating portions 102, arranged on the column conveyance path 103a. The conveyor 103 is then driven to convey the various-substance holders 50 along the conveyance path. Once the tip accommodating portions 102 reach the position of the row conveyance path 103b, the separate nozzle 117 is moved to the reagent accommodating portion 77, which accommodates the predetermined reagent. The separate nozzle 117 sucks the predetermined reagent, and then moves to a selected one of the various-substance holders 50 in the eight tip accommodating portions 102 stopped along the row conveyance path 103b. The separate nozzle 117 then dispenses the predetermined reagent through the installing opening 44 in the various-substance holder 50. Then, at the measurement point 104, provided on the conveyance path, the light receiving portion 106 receives light from the particles 17. At this time, the reacted allergen substance can be identified on the basis of the combination of labeling information on each of the particles 17 obtained from the signal based on the first label and the signal based on the second label.

Figure 12:
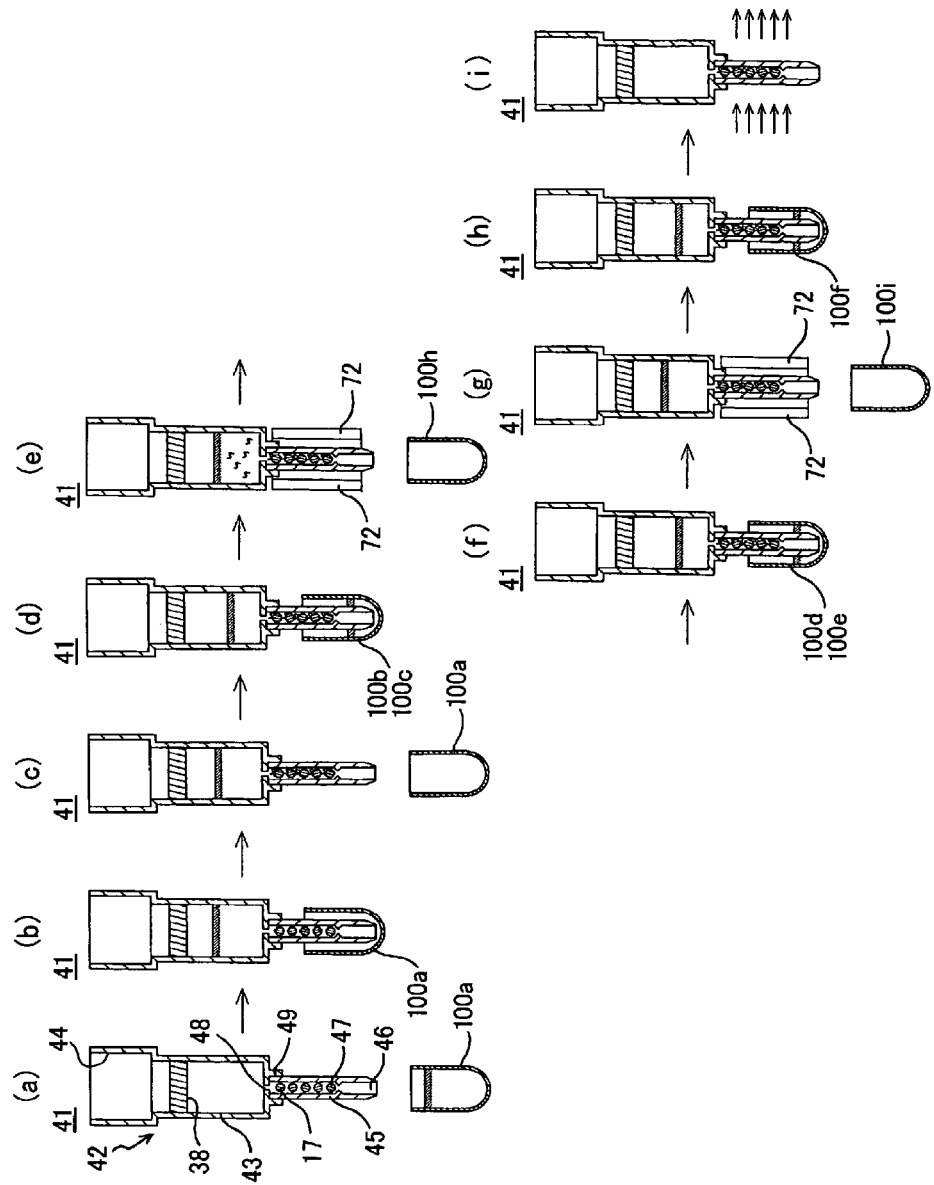
FIG. 12 is a flowchart showing a method for treating a various-substance holder according to a fourteenth embodiment.

With reference to FIG. 12, description will be given of a various-substance holder treating method according to a fourteenth embodiment using the various-substance holder 41 in conjunction with an example in which protein is immobilized and analyzed. In this treatment, oligonucleotides having several types (in this example, five types) of protein expressing base sequences and a protein capturing substance that captures expressed protein as shown in FIG. 12(a) are immobilized to the respective particles 17 shown in FIG. 4(b). The particles 17 to which the five types of protein expressing base sequences are immobilized are further labeled with five mutually-identifiable different types of fluorescent substances selected from, for example, the above-described fluorescent substances, so that the particles 17 are mutually identifiable. Here, the light from the fluorescent substances used to mutually identify the particles 17 corresponds to the signal based on the first label. For immobilization of these substances, a functional group is pre-generated or -expressed on the surface of each of the particles 17. This allows checks for the amount of protein expressed and bondability to a particular protein. In this example, the five types of particles 17 are accommodated in the capillary 45 of each of the eight tip-like containers 42 in an arbitrary or optional order. The capillary 45 with the particles 17 accommodated therein is fitted into the fitting portion 49, formed at the lower end of the thick tube 43. The capillary 45 is then attached to the fitting portion 49 by bonding or welding, to form the eight various-substance holders 41.

On the other hand, a solution of amino acid, ribosome, or the like is accommodated in the liquid holding portion 100a of each of the eight cartridge containers 100, provided in the various-substance holder treatment area 81. A cleaning fluid (hereinafter referred "PBS-T") made of a PBS buffer solution and a 0.05% Tween 20 buffer solution that is a surfactant is accommodated in the liquid accommodating portions 100b to 100g. A suspension of PBS-T and 5% skim milk is accommodated in the liquid accommodating portion 100h. A solution of an antibody labeled with a chemiluminescent substance and a biotinated substance is accommodated in the liquid accommodating portion 100i. Naturally, the chemiluminescent substance used for labeling is different from the five types of fluorescent substances identifying the base sequences immobilized to the particles 17. A signal from the chemiluminescent substance corresponds to the signal based on the second label.

In step S21, the installing opening 44, formed at the upper end of the thick tube 43 of the various-substance holder 41 thus formed, is installed on the nozzle 117 in the various-substance holder treating apparatus 80. Then, as shown in FIGS. 12(a), 12(b), and 12(c), the eight nozzles 117 in the nozzle head 84 of the various-substance holder treating apparatus 80 are moved to the liquid accommodating portions 100a of the cartridge container 100 in union. Each of the nozzles 117 then sucks the solution of amino acid or the like accommodated in the corresponding liquid accommodating portion 100a, into the capillary 45 at a speed s6 (for example, about 200 μlitters/sec) by an amount v6 (for example, about 500 μlitters). In this condition, the interior of the capillary 45 is heated by moving the heating wall 72, sandwiched between the heating plates 73 of the temperature increasing and reducing means 71, closer to the various-substance holder 41 so that the capillary 45 is sandwiched between the heating plates 73; the heating plates 73 are arranged like comb teeth. Thus, the interior of the capillary 45 is efficiently and reliably heated and maintained at 37.degree. C. for one hour.

In step S22, as shown in FIG. 12(d), the liquid is discharged from the capillary 45, and the nozzle head 84 is then moved to the liquid accommodating portion 100b. The capillary 45 is then cleaned by repeating the operation of sucking and discharging the PBS-T solution into and from the capillary 45, for example, 10 times at a speed s7 (for example, about 760 to 1,700 μlitters/sec) by an amount v7 (for example, about 500 μlitters). This operation is repeated on the liquid accommodating portion 100c.

In step S23, as shown in FIG. 12(e), the nozzle head 84 is moved to the liquid accommodating portion 100h to suck the suction of PBS-T and 5% skim milk. Reaction is allowed to occur at room temperature for about one hour for blocking.

In step S24, as shown in FIG. 12(f), the liquid is discharged from the capillary 45, and the nozzle head 84 is then moved to the liquid accommodating portion 100b. The capillary 45 is then cleaned by repeating the operation of sucking and discharging the PBS-T solution into and from the capillary 45, for example, 10 times at the speed s8 (for example, about 760 to 1,700 μlitters/sec) by the amount v8 (for example, about 500 μlitters). This operation is repeated on the liquid accommodating portion 100e.

In step S25, as shown in FIG. 12(g), the various-substance holder 41 is transferred to the liquid accommodating portion 100i to suck the suspension in which the antibody labeled with the chemiluminescent substance and the biotinated substance are suspended. Incubation is then allowed to occur at room temperature for about 30 minutes to one hour.

Moreover, in step S26, as shown in FIG. 12(h), the nozzle head 84 is transferred to the liquid accommodating portion 100f. The capillary 45 is then cleaned by repeating the operation of sucking and discharging the PBS-T solution into and from the capillary 45, for example, 10 times at the speed s3. This operation is repeated on the liquid accommodating portion 100g.

In step S27, as shown in FIG. 12(i), the nozzle head 84 is moved to the tip accommodating portions 102 stopped on the column conveyance path 103a of the conveyor 103. The various-substance holders 41 are then released, via the pawl 122a, from the plurality of (eight) batch nozzles (117), formed in the nozzle head 84. The various-substance holders 41 are then accommodated in the tip accommodating portions 102, arranged on the column conveyance path 103a. The conveyor 103 is then driven to convey the various-substance holders 41 along the conveyance path. Once the tip accommodating portions 102 reach the position of the row conveyance path 103b, the separate nozzle 117 is moved to the reagent accommodating portion 77. The separate nozzle 117 sucks the predetermined reagent, and then moves to a selected one of the various-substance holders 41 in the eight tip accommodating portions 102 stopped along the row conveyance path 103b. The separate nozzle 117 then dispenses a chemiluminescent substrate solution as the predetermined reagent through the installing opening 44 in the various-substance holder 41. Then, at the measurement point 104, provided on the conveyance path, the light receiving portion 106 receives and measures light from the particles 17. At this time, to allow signals based on the first label to be received, an excitation light pulse of a corresponding wavelength from the trigger light source 105 is turned on and emitted to each of the particles 17. The light receiving portion 106 receives the resulting light. While the pulse is off, the intensity of the signal based on the second labeling is measured for each particle. The measurements are thus performed under the pulse control by which the pulse is repeatedly turned on and off. On the basis of the intensity of the signal based on the first label and the intensity of the signal based on the second label, the protein having reacted with the antibody labeled with the chemiluminescent substance, the biotinated substance, or the like is identified, or the amount of protein expressed is measured.

Now, with reference to FIG. 13, description will be given of case where a various-substance holder treating method according to a fifteenth embodiment is applied to a SNPs detection reaction.

Figure 13:
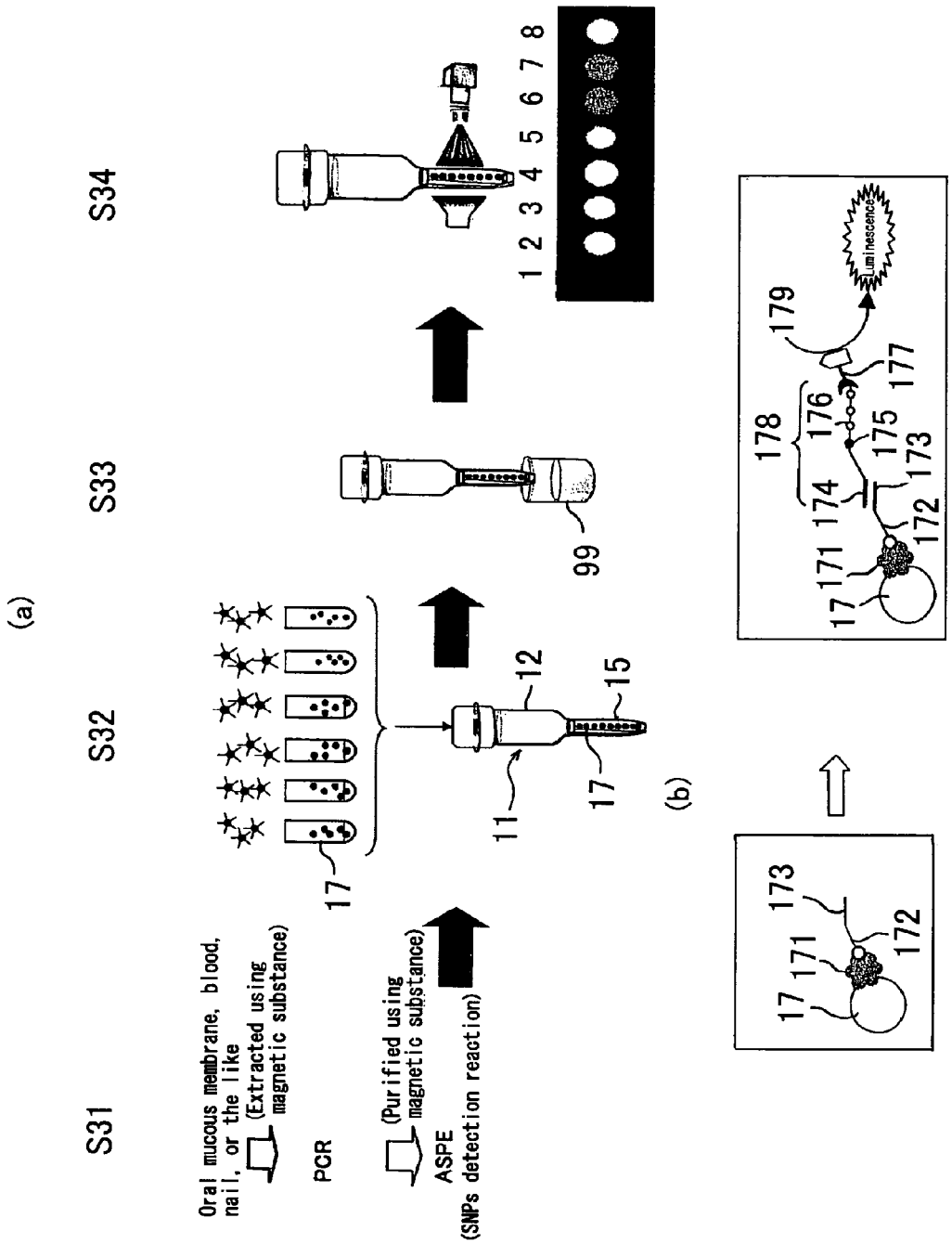
FIG. 13 is a flowchart showing a method for treating a various-substance holder according to a fifteenth embodiment.

As schematically shown in FIG. 13, this method is applied to a treatment for detecting polymorphism of a base (in this case, two variants of the base) at each of the SNPs (Single Nucleotide Polymorphisms) sites in four genes (ATase exon6, ATase exon8, CYP2C19 exon5, CYP2D6 exon1) from each of the samples collected from eight subjects. This treatment includes a sample preparing step S31 of extracting the genes from the samples, amplifying the extracted genes, and preparing ASPE products using an ASPE method described below, the sample preparing step serving as a preparation stage, an entrapping step S32 of bonding tag DNAs described below and serving as detecting probes, to particles to be entrapped in the capillary 15 of the tip-like container 12 of the various-substance holder 11 to prepare plural types (in this example, eight types) of particles 17 and entrapping the particles 17 in the capillary 15, a bonding and reaction step S33 of allowing the particles 17 to the ASPE products, and a detecting step S34 of detecting the result of the bonding reaction.

As shown in FIG. 13(a), the sample preparing step S31 includes a sampling step of collecting samples, for example, oral mucous membranes, blood, nails, or the like from eight subjects, an amplifying step of extracting DNAs contained in the oral mucous membranes or the like and amplifying each of the DNAs by a PCR method, a purifying step of purifying the DNAs, and an ASPE product preparing step of using the ASPE method described below to prepare the purified DNAs into ASPE products.

In the sampling step, for example, as shown in FIG. 13, the liquids in which the oral mucous membranes or the like collected from the eight subjects are accommodated in the cartridge containers 92, each having the eight well columns 92a. The tip-like containers 12 or dispensing tips of the various-substance holders 11 with the particles not entrapped in the capillaries 15 yet are installed on the nozzles 117 in the nozzle head 84. The nozzles 117 suck a suspension of magnetic particles the surface of which is covered with a porous substance or a substance such as silica and are transferred to each well column 92a. The nozzles 117 discharge and introduce the suspension into the well column 92a in union.

The driving plates 123 and the rods 112 are moved up and down to move the plungers 115a up and down to repeat the sucking and discharging operation. The DNAs are thus bonded to and captured by the magnetic particles. At this time, the eight magnets 122b are moved closer to the capillaries 15 of the eight various-substance holders 11 to apply magnetic fields to the interior of the capillaries 15. The magnetic particles having captured the DNAs are attracted to the inner wall of the capillary 15 of each of the tip-like containers 12 and thus separated from one another. The DNAs are dissociated and extracted from the separated magnetic particles having captured the DNAs and then accommodated in the well column 96 in the microplate.

Then, the DNAs extracted from the respective samples are amplified by the PCR method using a predetermined primer so as to obtain four DNAs. Each of the resulting DNAs is accommodated in a left one of the eight wells in the well column 99 in the microplate. The following operation is performed to remove foreign substances including residues such as the primer or the oral mucous membrane, from each well in which the suspension of the amplified DNAs is accommodated. A new tip-like container 12 is installed on the nozzle head 84. The plunger 115a is moved up and down to suck and discharge a new suspension of magnetic particles into and from the capillary to allow the DNAs to be captured by the magnetic particles. At this time, the comb teeth-like magnet 122b is used to apply a magnetic field to the interior of the tip-like container 12 to attract the magnetic particles to the inner wall of the tip-like container 12 for separation and purification.

Then, the ASPE (Allele-Specific Primer Extension method) is used to prepare ASPE products 178 required to determine the four SNPs sites in the genes in each of the samples.

As shown in FIG. 13(b), a synthetic DNA is used as a primer; the synthetic DNA has a base sequence 174 at a 3' terminal which is complementary to a base sequence 173 in a single-strand tag DNA 172 described below and a base 175 at a 5' terminal which is subjected to the SNP, the sequence between the base sequence 174 and the base 175 is designed to be complementary to a sequence closest to the SNP site in each of the four genes, and the synthetic DNA is made up of several tens of single-strand bases. Certain types of primers which are likely to be polymorphic, in this case, two types of primers for each of the four genes, a total of eight types of primers, are synthesized. Each primer contains one of eight different types of tag DNAs 172 having respective types of predetermined base sequences and a corresponding SNP base. Using Dig-dUTP 176 as a base instead of the base "T", an attempt is made to expand and amplify the primers by means of the PCR method on the basis of the genes in each of the samples. Then, only the primer corresponding to the type of polymorphism of the DNA from the sample is expanded and amplified. The ASPE product 178 is thus prepared for each of the eight samples.

The prepared ASPE product 178 for each sample is accommodated in a right well of the well column 99 on the matrix-like container 95. On the other hand, a cleaning fluid used in the detection step S34, described below, is accommodated in the eight wells 100a on the cartridge container 100. Moreover, the AP labeling anti-Dig antibody 177 that is specifically bonded to the Dig-dUTP 176 is accommodated in the eight wells 100b. Another cleaning fluid is accommodated in the eight wells 100c. A substrate solution 179 (CDP-Star) is accommodated in the reagent accommodating portion 77.

In this example, for each sample, all of the eight types of ASPE products 178 are mixed together and the mixture is accommodated in the well column 99. However, every two types of ASPE products 178 may be mixed together and the mixture may be accommodated in one of four different prepared well columns for treatment.

In step S32, the particles 17 to be accommodated in the various-substance holder 11 are produced and entrapped in the holder 11. As shown in FIG. 13(b), the particle 17 to be produced is, for example, coated with avidin 171 and bonded to the tag DNA 172 having the biotinated predetermined base sequence 173. Here, the particle 17 has such a size as a diameter of about 1 mm and may be composed of any of various resins, for example, nylon (manufactured by Polysciences). Alternatively, the particle 17 may be ceramics (manufactured by CHIBA CERAMIC MFG CO., LTD.; alumina of diameter 1.88 mm). If the light blocking particle is used, it may be composed of, for example, color glass of diameter 2.0 mm).

Furthermore, the base sequence 173 in each tag DNA 172 and the complimentary base sequence 174 contained in the primer are synthesized so that the polymorphic bases in the genes which are likely to be subjected to SNP have different base sequences 173 and 174. Then, in the treatment according to the present embodiment, the polymorphic base that is likely to be of two types at four SNP sites requires eight types of base sequences 173 and 174. Consequently, eight types of particles 17 are produced.

Before entrapment, the eight types of particles 17 are labeled with labeling substances such as pigments or dyes, for example, on the basis of colors (purple, navy blue, green, yellow, red, blue, brown, and orange) so as to be mutually identifiable for each type. The SNP sites in the different genes are pre-associated with the respective colors. For example, a "purple" particle and a "navy blue" particle are associated with the gene ATase exon6. Tag1 (base C) and Tag3 (base T) are used as the tag DNA 172. A "green" particle and a "yellow" particle are associated with the gene ATase exon8. Tag4 (base A) and Tag2 (base G) are used as the tag DNA 172. A "red" particle and a "blue" particle are associated with the gene CYP2C19 exon5. Tag7 (base A) and Tag (base G) are used as the tag DNA 172. A "brown" particle and an "orange" particle are arranged with the gene CYP2D6 exon1. Tag9 (base C) and Tag10 (base T) are used as the tag DNA 172.

The eight types of particles 17 thus produced into a set by bonding the eight types of tag DNAs 172 having the respective types of biotinated predetermined base sequences 173, to the particles 17, are entrapped in the capillary 15 of the tip-like container 12 in an arbitrary or optional order without the need to specify any sequence order. Eight various-substance holders 11 are thus produced, installed on the nozzle head 84, and arranged in a line. For entrapment, the set of the eight types of particles 17 is accommodated in the capillary 15 removed from the thick tube 13 of the tip-like container 12. Then, the lower end 18 of the thick tube 13 is fitted into the fitting portion 15a of the capillary 15. If the light-blocking particles are used, then for example, reacting particles and the light-blocking particles are alternately arranged.

The capillary 15 is made of, for example, polypropylene as described above. The size of the capillary 15 is such that for example, the capillary 15 is round and has a diameter of 1.1 mm when for example, the particles are made of ceramic and have a diameter of 1.0 mm. Furthermore, the capillary 15 is round and has a diameter of 2.0 mm when for example, the particles are made of ceramic and have a diameter of 1.88 mm. Moreover, when 2.0-mm glass beads are used as the light blocking particles, the capillary 15 is round and has a diameter of 2.2 mm.

In step S33, a moving portion (not shown) is used to move the nozzle head 84 to a position where the mouth portions 16 of the eight various-substance holders 11, arranged in the nozzle head 84 in a line, can be inserted into the respective wells in the well column 99 on the matrix-like container 95. Then, the moving portion (not shown) is used to insert the mouth portions 16 into the well column 99 on the matrix-like container 95 in union. Each of the plungers 115a is moved up and down relative to the various-substance holder 11 or moved up and down to repeat the sucking and discharging operation, to contact the mixed liquid of the ASPE products 178 accommodated for each sample with the particles 17 in the various-substance holder 11. Then, hybridization occur between the base sequence 173 in each of the tag DNAs 172 and the base sequence 174 in the corresponding one of the ASPE products 178 which is complementary to the base sequence 173. Each of the particles 17 having the corresponding ASPE products 178 is bonded to that ASPE product 178.

Then, in step S34, the moving portion (not shown) is used to move the nozzle head 84 to the second wells 100a on the cartridge container 100 in which the cleaning fluid is accommodated and to insert the mouth portions 16 into the second wells 100a in union. Each of the plungers 115a is then moved up and down to repeat the sucking and discharging operation for cleaning.

Subsequently, the nozzle head 84 is moved to the eight wells 100b on the cartridge container 100 in which the AP labeling anti-Dig antibody 177, bonding specifically to the Dig-dUTP 176, is accommodated. The mouth portions 16 are positioned over the eight wells 100b and then inserted into the wells 100b in union. Each of the plungers 115a is then used to repeat the sucking and discharging operation to bond the Dig-dUTP 176 to the AP labeling anti-Dig antibody 177. Then, for each sample, the particle 17 bonds to the ASPE product 178 of the type corresponding to the present polymorphism and to which the AP labeling anti-Dig antibody 177 is bonded. Moreover, the nozzle head 84 is moved to the well 100c on the cartridge container 100 to position the mouth portions 16 over the wells 100c. The mouth portions 16 are then inserted into the wells 100c in union to repeat the operation of sucking and discharging the accommodated cleaning fluid for cleaning.

Then, the moving portion (not shown) is used to further move the nozzle head 84 by a row distance in the row direction as the moving path. The various-substances 11 are removed from the nozzle head 84 and accommodated in the eight tip accommodating portions 102 arranged in the column direction at the positions corresponding to the mouth portions 16 in the nozzle head 84. The tip accommodating portions 102 are conveyed by the conveyor 103. When the eight tip accommodating portions 102 are placed in the row direction, the whole nozzle head 84 is moved so that the separate nozzle, provided away from the eight batch nozzles, from which the various-substance holders 11 have been removed, is located at the position where the dispensing tip 78 is accommodated. The nozzle head 84 is then lowered at that position to fit and install the dispensing tip 78 only on the separate nozzle. The nozzle head 84 is further moved to position the dispensing tip 78 over the reagent accommodating portion 77 to suck the substrate solution from the reagent accommodating portion 77 into the dispensing tip 78.

The moving portion (not shown) is used to move the nozzle head 84 to dispense the substrate solution 179 through the installing openings 14 into the eight various-substance holders 11 accommodated in the tip accommodating portions 102 arranged in the row direction. The eight various-substance holders 11 are also conveyed along the conveyance path by the conveyor 103. Then, chemiluminescence resulting from the reaction between the substrate solution 179 and the Dig is sequentially detected at the measurement point 104 for the eight samples.

FIG. 13 shows, at step S34, a photograph showing the result of measurement of the genes in one of the eight samples. It is assumed that the particles 17 entrapped in the various-substance holder 11 for this sample happened to be arranged in the above-described order of colors (purple, navy blue, green, yellow, red, blue, brown, and orange) from the first particle 17 to the eighth particle 17. Then, the figure shows that for the genes in the sample, only a very weak luminescence was detected for the first particle (purple), the sixth particle (blue), and the seventh particle (brown). This indicates that the SNP site of the gene ATase exon6 in the sample is the base T, the SNP site of the gene ATase exon8 is the base A/G, the SNP site of the gene CYP2C19 exon5 is the base A, and the SNP site of the gene CYP2D6 exon1 is the base T.

n the above-described example, the Dig-dUTP and the AP labeling anti-Dig antibody, which bonds specifically to the Dig-dUDP, are used. However, for example, an HRP labeling anti-Dig antibody or a POD labeling anti-Dig antibody may be used in place of the AP labeling anti-Dig antibody.

The specific description of the embodiments is to enable better understanding of the present invention well and is not to limit different embodiments. Accordingly, the embodiments may be varied as long as the spirit of the present invention is not changed. For example, in the embodiments, only the cases of the DNA, allergen substance, and protein have been described. However, a sugar chain, another DNA substance, RNA, or the like may be used. Furthermore, in the above description, the particulate carriers are spherical particles and the plurality of particulate carriers have the same diameter. However, the present invention is not limited to this. The particles may each be shaped like a cylinder or a rectangular parallelepiped. The size of the particles may vary. The present invention is also applicable to amorphous particulate carriers. Furthermore, the numerical values, numbers of times, shapes, numbers of components, amounts of substances, and the like which are used in the above description are not limitative. In short, any particulate carriers may be used provided that the particulate carriers are formed to have a size and a shape appropriate to pass through the mouth portion and the installing opening, and when held in the carrier holding portion, allow the suction and discharge of the fluid.

Moreover, the above description relates only to the case where the particulate carriers are one-dimensionally arranged. However, the present invention is not limited to this. However, the one-dimensional arrangement enables reliable measurements because a sequence of chemical substances can be reliably associated with the one-dimensional path. Furthermore, the above description relates only to the case where the particulate carriers are accommodated in the capillary. However, it is possible to provide a core provided in the thick tube or the storage portion and to form a groove or a projection on an outer wall of the core or the inner wall of the thick tube or storage portion so as to form a passage so that the particulate carriers can be stored in the passage.

It is also possible to optionally combine the above-described components, particulate carriers, capillaries, tip-like container, nozzle head, entrapping portion, nozzles, heating means, or devices, which may be appropriately varied as required. Moreover, the ligand is not limited to the DNA but may be a genetic substance such as oligonucleotide or RNA, an immune substance, a protein, a sugar chain, pheromone, allomone, mitochondria, a virus, or a plasmid.

Furthermore, the above-described reagents and substances are illustrative and other reagents and substances may be used. Additionally, the carriers having captured DNAs or the like may be taken out of the capillary or the like, stored, and used for another treatment.

INDUSTRIAL APPLICABILITY

The present invention relates to the various-substance holder, various-substance holder treating apparatus, and various-substance holder treating method. The present invention relates to every field including those requiring handling of biological macromolecules or small molecules such as genes, immune systems, amino acids, proteins, and sugars, for example, industrial fields, agricultural fields such as foods, agriculture, and fishery processing, medical fields such as sanitation, healthcare, immunity, diseases, and heredity, and scientific fields such as chemistry or biology.

The present invention provides a method that is particularly effective for consecutively performing a series of treatments using a large number of reagents and substances, in a predetermined order.

The invention claimed is:

1. A various-substance holder treating apparatus comprising:
   a nozzle head having one or more nozzles through which gas is sucked and discharged,
   a suction and discharge mechanism that sucks and discharges the gas via the nozzle,
   one or more various-substance holders each having a plurality of particulate carriers or plural sets of the particulate carriers to which one type selected from plural types of chemical substances are or can be immobilized respectively and a carrier holding portion one-dimensionally holding the plurality of particulate carriers or the plural sets of particulate carriers in a straight line in a substantially stationary state such that the plurality of particulate carriers or the plural sets of the particulate carriers can be externally measured and being or capable of being installed in the nozzle, wherein each of the plurality of particulate carriers or at least one of the particulate carriers belonging to the plural sets of the particulate carriers are labeled according to types of the chemical substances or for each of the particulate carriers or each set of the particulate carriers so as to be mutually identifiable before the particulate carriers are introduced and held in the carrier holding portion, a temperature increasing and reducing member which is provided outside the carrier holding portion and which is movable, relative to the various-substance holder, such that the member can be placed close to or in contact with the carrier holding portion by moving the member relative to the various-substance holder, the temperature increasing and reducing member increasing or reducing temperature in response to an external signal, a liquid accommodating portion group that accommodates or can accommodate various liquids, and a horizontal moving mechanism configured to move the temperature increasing and reducing member, together with the nozzle head, horizontally and relative to the liquid accommodating portion group, wherein the carrier holding portion includes a tip-like container having an installing opening that can be installed around a nozzle through which gas is sucked and discharged, and a mouth portion through which a fluid is allowed to flow in and out by sucking and discharging the gas, wherein the tip-like container has a storage portion which can store liquid and which has the installing opening, and a capillary which is in communication with the storage portion and which has the mouth portion, the capillary being formed to be thinner than the storage portion, and the particulate carriers are held in the capillary wherein, when the tip-like container is installed around the nozzle, the tip-like container extends from the nozzle in a vertical direction;

the various-substance holder treating apparatus further comprises:

a housing in which the temperature increasing and reducing member is provided;

a motor connected to the housing and configured to cause the temperature increasing and reducing member to move, relative to each of the various-substance holder and the housing, in another a horizontal direction that is perpendicular to the vertical direction of extension of the tip-like container such that the temperature increasing and reducing member can be placed close to or in contact with the carrier holding portion; and a vertical movement mechanism configured to move the nozzle head vertically and relative to each of the housing, the temperature increasing and reducing member, and the liquid accommodating portion group, wherein at least a portion of the vertical movement mechanism is contained in the housing; and wherein the horizontal moving mechanism is configured to move the housing, together with each of the nozzle head, the temperature increasing and reducing member, the motor, and the vertical movement mechanism, horizontally and relative to the liquid accommodating portion group.

2. The various-substance holder treating apparatus according to claim 1, further comprising a control section that controls amount, speed, count, time, or position of suction and discharge performed by the nozzle on the basis of substance conditions including a structure of the various-substance holder, types and concentrations of various substances which are immobilized to the particulate carriers or which are present in the fluid, amount of the liquid, and coordinate positions including a position where the liquid is accommodated, as well as a content of a treatment.

3. The various-substance holder treating apparatus according to claim 1, comprising a receiving device that receives signals from the particulate carriers held by the carrier holding portion and an analyzing device that performs analysis on the basis of the signals from the receiving device.

4. The various-substance holder treating apparatus according to claim 2, wherein the nozzle head has a plurality of batch nozzles and one separate nozzle arranged in a column direction, and the suction and discharge mechanism allows gas to be sucked into and discharged from the batch nozzles and separate nozzle in the nozzle head at a time, and wherein the moving means has nozzle head moving means for moving the nozzle head along a row direction relative to a stage having the liquid accommodating portion group, and a row and column path conveying means having a closed, substantially quadrangular conveyance path including two column conveyance paths located on a moving path of the batch nozzles and extending along the column direction and two row conveyance paths located on a moving path of the separate nozzle and extending along the row direction, the row and column path conveying means conveying, along the conveyance path, a conveying and accommodating portion capable of accommodating the tip-like containers removed from the batch nozzles or a liquid discharged from the batch nozzle head.

5. The various-substance holder treating apparatus according to claim 4, comprising receiving means for receiving a signal from the removed tip-like container or the conveying and accommodating portion, the receiving means being provided at a predetermined position along the conveyance path of the row and column path conveying means.

6. The various-substance holder treating apparatus according to claim 1, wherein the temperature increasing and reducing member is a conductive member.

7. The various-substance holder treating apparatus according to claim 1, wherein the temperature increasing and reducing member comprises:

a heating wall; and at least two heating plates mounted on the heating wall so that the tip-like container is located between the at least two heating plates.

* * * * *